US009259265B2

(12) United States Patent
Harris et al.

(10) Patent No.: US 9,259,265 B2
(45) Date of Patent: Feb. 16, 2016

(54) SURGICAL INSTRUMENTS FOR TENSIONING TISSUE

(75) Inventors: Jason L. Harris, Mason, OH (US);
Jeffrey S. Swayze, Hamilton, OH (US);
Foster B. Stulen, Mason, OH (US);
Gregory W. Johnson, Milford, OH (US); Prasanna Malaviya, Mason, OH (US); Paul Guerra, Los Gatos, CA (US)

(73) Assignee: Ethicon Endo-Surgery, LLC, Guaynabo, Puerto Rico ( * ) Notice: Subject to any disclaimer, the term of this patent is extended or adjusted under 35 U.S.C. 154(b) by 1183 days.

(21) Appl. No.: 13/189,169

(22) Filed: Jul. 22, 2011

(65) Prior Publication Data
US 2013/0023875 A1   Jan. 24, 2013

(51) Int. Cl.
*A61B 18/14* (2006.01)
*A61B 18/00* (2006.01)

(52) U.S. Cl.
CPC ..... *A61B 18/1445* (2013.01); *A61B 2018/0063* (2013.01); *A61B 2018/00184* (2013.01);
(Continued)

(58) Field of Classification Search
CPC ............ A61B 18/085; A61B 18/1442; A61B 18/1445; A61B 18/1447; A61B 18/1482; A61B 2018/00083; A61B 2018/00345; A61B 2018/00351; A61B 2018/00404; A61B 2018/00428; A61B 2018/00577; A61B 2018/00589; A61B 2018/00595; A61B 2018/00601; A61B 2018/00607; A61B 2018/00619; A61B 2018/0063; A61B 2018/00642; A61B 2018/0072; A61B 2018/00791; A61B 2018/00827; A61B 2018/00892; A61B 2018/126; A61B 2018/1412; A61B 2018/1452; A61B 2018/1455; A61B 2018/1462; A61B 2018/1465; A61B 2018/1475; A61B 2018/1495; A61B 2018/1961; A61B 17/320092; A61B 17/2816; A61B 17/28; A61B 17/29; A61B 17/12013; A61B 17/2202; A61B 17/3201; A61B 2017/00734; A61B 2017/2902; A61B 2017/2926; A61B 2017/2927; A61B 2017/2947; A61B 2017/320052; A61B 2017/2948
USPC .............................. 606/51–52, 169, 205–207
See application file for complete search history.

(56) References Cited

U.S. PATENT DOCUMENTS 2,366,274 A   1/1945   Luth et al.
2,458,152 A   1/1949   Eakins
(Continued)

FOREIGN PATENT DOCUMENTS

DE   20004812 U1   9/2000
DE   10201569 A1   7/2003
(Continued)

OTHER PUBLICATIONS

Humphrey, J.D., "Continuum Thermomechanics and the Clinical Treatment of Disease and Injury," Appl. Mech. Rev., vol. 56, No. 2 pp. 231-260 (Mar. 2003).
(Continued)

*Primary Examiner* — Jaymi Della
*Assistant Examiner* — Khadijeh Vahdat

(57) ABSTRACT

A surgical instrument can comprise an end effector including a plurality of jaws which can be configured to compress tissue therebetween. The end effector can further comprise one or more electrodes which can be configured to direct a flow of electrical current through the tissue in order to heat the tissue and denature collagen and/or other proteins within the tissue. As the tissue cools, the collagen and/or other proteins can renature and thereby seal the tissue. In certain embodiments, the end effector of the surgical instrument can further comprise movable portions which can apply a tension force to the tissue surrounding the tissue being sealed. In various circumstances, the tension force can reduce the over-denaturation, shrinkage, and/or other damage to the surrounding tissue caused by heat flowing from the end effector during the sealing process.

20 Claims, 18 Drawing Sheets

(52) U.S. Cl.
CPC .......... *A61B2018/00642* (2013.01); *A61B 2018/00702* (2013.01); *A61B 2018/00791* (2013.01); *A61B 2018/00815* (2013.01); *A61B 2018/1455* (2013.01)

(56) References Cited

U.S. PATENT DOCUMENTS

| | | |
|---|---|---|
| 2,510,693 A | 6/1950 | Green |
| 3,166,971 A | 1/1965 | Stoecker |
| 3,580,841 A | 5/1971 | Cadotte et al. |
| 3,703,651 A | 11/1972 | Blowers |
| 4,005,714 A | 2/1977 | Hiltebrandt |
| 4,058,126 A | 11/1977 | Leveen |
| 4,220,154 A | 9/1980 | Semm |
| 4,237,441 A | 12/1980 | van Konynenburg et al. |
| 4,281,785 A | 8/1981 | Brooks |
| 4,304,987 A | 12/1981 | van Konynenburg |
| 4,545,926 A | 10/1985 | Fouts, Jr. et al. |
| 4,582,236 A | 4/1986 | Hirose |
| 4,761,871 A | 8/1988 | O'Connor et al. |
| 4,849,133 A | 7/1989 | Yoshida et al. |
| 4,910,389 A | 3/1990 | Sherman et al. |
| 5,104,025 A | 4/1992 | Main et al. |
| 5,106,538 A | 4/1992 | Barma et al. |
| 5,108,383 A | 4/1992 | White |
| 5,205,459 A | 4/1993 | Brinkerhoff et al. |
| 5,285,945 A | 2/1994 | Brinkerhoff et al. |
| 5,309,927 A | 5/1994 | Welch |
| 5,387,207 A | 2/1995 | Dyer et al. |
| 5,389,098 A | 2/1995 | Tsuruta et al. |
| 5,395,312 A | 3/1995 | Desai |
| 5,403,312 A | 4/1995 | Yates et al. |
| 5,428,504 A | 6/1995 | Bhatla |
| 5,496,317 A | 3/1996 | Goble et al. |
| 5,504,650 A | 4/1996 | Katsui et al. |
| 5,511,556 A | 4/1996 | DeSantis |
| 5,522,839 A | 6/1996 | Pilling |
| 5,558,671 A | 9/1996 | Yates |
| 5,563,179 A | 10/1996 | Stone et al. |
| 5,599,350 A | 2/1997 | Schulze et al. |
| 5,624,452 A | 4/1997 | Yates |
| 5,647,871 A | 7/1997 | Levine et al. |
| 5,665,085 A | 9/1997 | Nardella |
| 5,665,100 A | 9/1997 | Yoon |
| 5,674,220 A | 10/1997 | Fox et al. |
| 5,688,270 A | 11/1997 | Yates et al. |
| 5,693,051 A | 12/1997 | Schulze et al. |
| 5,709,680 A | 1/1998 | Yates et al. |
| 5,716,366 A | 2/1998 | Yates |
| 5,735,848 A | 4/1998 | Yates et al. |
| 5,752,973 A | 5/1998 | Kieturakis |
| 5,755,717 A | 5/1998 | Yates et al. |
| 5,762,255 A | 6/1998 | Chrisman et al. |
| 5,797,941 A | 8/1998 | Schulze et al. |
| 5,800,432 A | 9/1998 | Swanson |
| 5,807,393 A | 9/1998 | Williamson, IV et al. |
| 5,810,811 A | 9/1998 | Yates et al. |
| 5,817,033 A | 10/1998 | DeSantis et al. |
| 5,817,093 A | 10/1998 | Williamson, IV et al. |
| 5,880,668 A | 3/1999 | Hall |
| 5,906,625 A | 5/1999 | Bito et al. |
| 5,984,938 A | 11/1999 | Yoon |
| 6,003,517 A | 12/1999 | Sheffield et al. |
| 6,013,052 A | 1/2000 | Durman et al. |
| 6,063,098 A | 5/2000 | Houser et al. |
| 6,068,629 A | 5/2000 | Haissaguerre et al. |
| 6,074,389 A | 6/2000 | Levine et al. |
| 6,099,550 A | 8/2000 | Yoon |
| H1904 H | 10/2000 | Yates et al. |
| 6,206,876 B1 | 3/2001 | Levine et al. |
| 6,292,700 B1 | 9/2001 | Morrison et al. |
| 6,340,878 B1 | 1/2002 | Oglesbee |
| H2037 H | 7/2002 | Yates et al. |
| 6,443,968 B1 | 9/2002 | Holthaus et al. |
| 6,464,702 B2 | 10/2002 | Schulze et al. |
| 6,500,176 B1 | 12/2002 | Truckai et al. |
| 6,503,248 B1 | 1/2003 | Levine |
| 6,514,252 B2 | 2/2003 | Nezhat et al. |
| 6,517,565 B1 | 2/2003 | Whitman et al. |
| 6,533,784 B2 | 3/2003 | Truckai et al. |
| 6,554,829 B2 | 4/2003 | Schulze et al. |
| 6,558,376 B2 | 5/2003 | Bishop |
| 6,572,639 B1 | 6/2003 | Ingle et al. |
| 6,575,969 B1 | 6/2003 | Rittman, III et al. |
| 6,589,200 B1 | 7/2003 | Schwemberger et al. |
| 6,602,252 B2 | 8/2003 | Mollenauer |
| 6,635,057 B2 | 10/2003 | Harano et al. |
| 6,656,177 B2 | 12/2003 | Truckai et al. |
| 6,656,198 B2 | 12/2003 | Tsonton et al. |
| 6,673,248 B2 | 1/2004 | Chowdhury |
| 6,679,882 B1 | 1/2004 | Kornerup |
| 6,722,552 B2 | 4/2004 | Fenton, Jr. |
| 6,770,072 B1 | 8/2004 | Truckai et al. |
| 6,773,409 B2 | 8/2004 | Truckai et al. |
| 6,789,939 B2 | 9/2004 | Schrödinger et al. |
| 6,800,085 B2 | 10/2004 | Selmon et al. |
| 6,802,843 B2 | 10/2004 | Truckai et al. |
| 6,811,842 B1 | 11/2004 | Ehrnsperger et al. |
| 6,821,273 B2 | 11/2004 | Mollenauer |
| 6,860,880 B2 | 3/2005 | Treat et al. |
| 6,905,497 B2 | 6/2005 | Truckai et al. |
| 6,908,463 B2 | 6/2005 | Treat et al. |
| 6,913,579 B2 | 7/2005 | Truckai et al. |
| 6,926,716 B2 | 8/2005 | Baker et al. |
| 6,929,622 B2 | 8/2005 | Chian |
| 6,929,644 B2 | 8/2005 | Truckai et al. |
| 6,953,461 B2 | 10/2005 | McClurken et al. |
| 7,000,818 B2 | 2/2006 | Shelton, IV et al. |
| 7,011,657 B2 | 3/2006 | Truckai et al. |
| 7,041,102 B2 | 5/2006 | Truckai et al. |
| 7,066,936 B2 | 6/2006 | Ryan |
| 7,070,597 B2 | 7/2006 | Truckai et al. |
| 7,083,619 B2 | 8/2006 | Truckai et al. |
| 7,087,054 B2 | 8/2006 | Truckai et al. |
| 7,101,372 B2 | 9/2006 | Dycus et al. |
| 7,112,201 B2 | 9/2006 | Truckai et al. |
| 7,125,409 B2 | 10/2006 | Truckai et al. |
| 7,143,925 B2 | 12/2006 | Shelton, IV et al. |
| 7,147,138 B2 | 12/2006 | Shelton, IV |
| 7,156,846 B2 | 1/2007 | Dycus et al. |
| 7,169,146 B2 | 1/2007 | Truckai et al. |
| 7,169,156 B2 | 1/2007 | Hart |
| 7,186,253 B2 | 3/2007 | Truckai et al. |
| 7,189,233 B2 | 3/2007 | Truckai et al. |
| 7,207,471 B2 | 4/2007 | Heinrich et al. |
| 7,220,951 B2 | 5/2007 | Truckai et al. |
| 7,225,964 B2 | 6/2007 | Mastri et al. |
| 7,235,073 B2 | 6/2007 | Levine et al. |
| 7,307,313 B2 | 12/2007 | Ohyanagi et al. |
| 7,309,849 B2 | 12/2007 | Truckai et al. |
| 7,311,709 B2 | 12/2007 | Truckai et al. |
| 7,329,257 B2 | 2/2008 | Kanehira et al. |
| 7,354,440 B2 | 4/2008 | Truckal et al. |
| 7,371,227 B2 | 5/2008 | Zeiner |
| 7,381,209 B2 | 6/2008 | Truckai et al. |
| 7,396,356 B2 | 7/2008 | Mollenauer |
| 7,404,508 B2 | 7/2008 | Smith et al. |
| 7,407,077 B2 | 8/2008 | Ortiz et al. |
| 7,435,582 B2 | 10/2008 | Zimmermann et al. |
| 7,445,621 B2 | 11/2008 | Dumbauld et al. |
| 7,464,846 B2 | 12/2008 | Shelton, IV et al. |
| 7,488,319 B2 | 2/2009 | Yates |
| 7,510,107 B2 | 3/2009 | Timm et al. |
| 7,513,025 B2 | 4/2009 | Fischer |
| 7,550,216 B2 | 6/2009 | Ofer et al. |
| 7,559,452 B2 | 7/2009 | Wales et al. |
| 7,588,176 B2 | 9/2009 | Timm et al. |
| 7,597,693 B2 | 10/2009 | Garrison |
| 7,604,150 B2 | 10/2009 | Boudreaux |
| 7,628,792 B2 | 12/2009 | Guerra |
| 7,641,671 B2 | 1/2010 | Crainich |
| 7,644,848 B2 | 1/2010 | Swayze et al. |
| 7,658,311 B2 | 2/2010 | Boudreaux |
| 7,665,647 B2 | 2/2010 | Shelton, IV et al. |

(56) References Cited

U.S. PATENT DOCUMENTS

| | | |
|---|---|---|
| 7,666,206 B2 | 2/2010 | Taniguchi et al. |
| 7,703,459 B2 | 4/2010 | Saadat et al. |
| 7,708,751 B2 | 5/2010 | Hughes et al. |
| 7,722,607 B2 | 5/2010 | Dumbauld et al. |
| 7,753,904 B2 | 7/2010 | Shelton, IV et al. |
| 7,762,445 B2 | 7/2010 | Heinrich et al. |
| 7,766,910 B2 | 8/2010 | Hixson et al. |
| 7,776,037 B2 | 8/2010 | Odom |
| 7,780,663 B2 | 8/2010 | Yates et al. |
| 7,784,663 B2 | 8/2010 | Shelton, IV |
| 7,815,641 B2 | 10/2010 | Dodde et al. |
| 7,819,298 B2 | 10/2010 | Hall et al. |
| 7,832,408 B2 | 11/2010 | Shelton, IV et al. |
| 7,832,612 B2 | 11/2010 | Baxter, III et al. |
| 7,879,035 B2 | 2/2011 | Garrison et al. |
| 7,879,070 B2 | 2/2011 | Ortiz et al. |
| 7,931,649 B2 | 4/2011 | Couture et al. |
| 7,935,114 B2 | 5/2011 | Takashino et al. |
| 7,955,331 B2 | 6/2011 | Truckai et al. |
| 7,963,963 B2 | 6/2011 | Francischelli et al. |
| 7,981,113 B2 | 7/2011 | Truckai et al. |
| 8,070,036 B1 | 12/2011 | Knodel |
| 8,136,712 B2 | 3/2012 | Zingman |
| 8,141,762 B2 | 3/2012 | Bedi et al. |
| 8,157,145 B2 | 4/2012 | Shelton, IV et al. |
| 8,246,618 B2 | 8/2012 | Bucciaglia et al. |
| 8,298,232 B2 | 10/2012 | Unger |
| 2002/0165541 A1 | 11/2002 | Whitman |
| 2003/0069579 A1* | 4/2003 | Truckai et al. .................. 606/48 |
| 2003/0105474 A1 | 6/2003 | Bonutti |
| 2003/0114851 A1* | 6/2003 | Truckai et al. .................. 606/51 |
| 2003/0130693 A1 | 7/2003 | Levin et al. |
| 2003/0158548 A1 | 8/2003 | Phan et al. |
| 2003/0216722 A1 | 11/2003 | Swanson |
| 2004/0019350 A1 | 1/2004 | O'Brien et al. |
| 2004/0138621 A1 | 7/2004 | Jahns et al. |
| 2004/0193150 A1 | 9/2004 | Sharkey et al. |
| 2004/0232196 A1 | 11/2004 | Shelton, IV et al. |
| 2005/0085809 A1 | 4/2005 | Mucko et al. |
| 2005/0165429 A1 | 7/2005 | Douglas et al. |
| 2005/0203507 A1 | 9/2005 | Truckai et al. |
| 2005/0261581 A1 | 11/2005 | Hughes et al. |
| 2005/0267464 A1 | 12/2005 | Truckai et al. |
| 2006/0052778 A1 | 3/2006 | Chapman et al. |
| 2006/0064086 A1 | 3/2006 | Odom |
| 2006/0069388 A1 | 3/2006 | Truckai et al. |
| 2006/0159731 A1 | 7/2006 | Shoshan |
| 2006/0217709 A1 | 9/2006 | Couture et al. |
| 2007/0027469 A1 | 2/2007 | Smith et al. |
| 2007/0073341 A1 | 3/2007 | Smith et al. |
| 2007/0106158 A1 | 5/2007 | Madan et al. |
| 2007/0146113 A1 | 6/2007 | Truckai et al. |
| 2007/0191713 A1 | 8/2007 | Eichmann et al. |
| 2007/0208312 A1 | 9/2007 | Norton et al. |
| 2007/0232920 A1 | 10/2007 | Kowalski et al. |
| 2007/0232926 A1 | 10/2007 | Stulen et al. |
| 2007/0232927 A1 | 10/2007 | Madan et al. |
| 2007/0232928 A1 | 10/2007 | Wiener et al. |
| 2007/0239025 A1 | 10/2007 | Wiener et al. |
| 2007/0260242 A1 | 11/2007 | Dycus et al. |
| 2008/0071269 A1 | 3/2008 | Hilario et al. |
| 2008/0147062 A1 | 6/2008 | Truckai et al. |
| 2008/0167522 A1 | 7/2008 | Giordano et al. |
| 2008/0188851 A1 | 8/2008 | Truckai et al. |
| 2008/0221565 A1 | 9/2008 | Eder et al. |
| 2008/0262491 A1 | 10/2008 | Swoyer et al. |
| 2008/0294158 A1 | 11/2008 | Pappone et al. |
| 2009/0048589 A1 | 2/2009 | Takashino et al. |
| 2009/0076506 A1 | 3/2009 | Baker |
| 2009/0076534 A1 | 3/2009 | Shelton, IV et al. |
| 2009/0099582 A1 | 4/2009 | Isaacs et al. |
| 2009/0125027 A1 | 5/2009 | Fischer |
| 2009/0206140 A1 | 8/2009 | Scheib et al. |
| 2009/0209979 A1 | 8/2009 | Yates et al. |
| 2009/0248002 A1 | 10/2009 | Takashino et al. |
| 2009/0320268 A1 | 12/2009 | Cunningham et al. |
| 2010/0010299 A1 | 1/2010 | Bakos et al. |
| 2010/0032470 A1 | 2/2010 | Hess et al. |
| 2010/0036370 A1 | 2/2010 | Mirel et al. |
| 2010/0036380 A1 | 2/2010 | Taylor et al. |
| 2010/0036405 A1 | 2/2010 | Giordano et al. |
| 2010/0081863 A1 | 4/2010 | Hess et al. |
| 2010/0081864 A1 | 4/2010 | Hess et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0094323 A1 | 4/2010 | Isaacs et al. |
| 2010/0237132 A1 | 9/2010 | Measamer et al. |
| 2010/0264194 A1 | 10/2010 | Huang et al. |
| 2011/0087208 A1 | 4/2011 | Boudreaux et al. |
| 2011/0087209 A1 | 4/2011 | Boudreaux et al. |
| 2011/0087218 A1 | 4/2011 | Boudreaux et al. |
| 2011/0087219 A1 | 4/2011 | Boudreaux et al. |
| 2011/0087220 A1 | 4/2011 | Felder et al. |
| 2011/0155781 A1 | 6/2011 | Swensgard et al. |
| 2011/0238065 A1 | 9/2011 | Hunt et al. |
| 2011/0251608 A1 | 10/2011 | Timm et al. |
| 2011/0251609 A1 | 10/2011 | Johnson et al. |
| 2011/0251612 A1 | 10/2011 | Faller et al. |
| 2011/0251613 A1 | 10/2011 | Guerra et al. |
| 2011/0264093 A1 | 10/2011 | Schall |
| 2011/0276057 A1 | 11/2011 | Conlon et al. |
| 2011/0282339 A1 | 11/2011 | Weizman et al. |
| 2011/0306963 A1* | 12/2011 | Dietz et al. ...................... 606/41 |
| 2011/0306964 A1 | 12/2011 | Stulen et al. |
| 2011/0306965 A1 | 12/2011 | Norvell et al. |
| 2011/0306966 A1 | 12/2011 | Dietz et al. |
| 2011/0306967 A1 | 12/2011 | Payne et al. |
| 2011/0306968 A1 | 12/2011 | Beckman et al. |
| 2011/0306972 A1 | 12/2011 | Widenhouse et al. |
| 2011/0306973 A1 | 12/2011 | Cummings et al. |
| 2012/0010615 A1 | 1/2012 | Cummings et al. |
| 2012/0010616 A1 | 1/2012 | Huang et al. |
| 2012/0012636 A1 | 1/2012 | Beckman et al. |
| 2012/0012638 A1 | 1/2012 | Huang et al. |
| 2012/0016413 A1 | 1/2012 | Timm et al. |
| 2012/0022519 A1 | 1/2012 | Huang et al. |
| 2012/0022524 A1 | 1/2012 | Timm et al. |
| 2012/0022525 A1 | 1/2012 | Dietz et al. |
| 2012/0022526 A1 | 1/2012 | Aldridge et al. |
| 2012/0022527 A1 | 1/2012 | Woodruff et al. |
| 2012/0022528 A1 | 1/2012 | White et al. |
| 2012/0022529 A1 | 1/2012 | Shelton, IV et al. |
| 2012/0022530 A1 | 1/2012 | Woodruff et al. |
| 2012/0101488 A1 | 4/2012 | Aldridge et al. |
| 2012/0150176 A1 | 6/2012 | Weizman |

FOREIGN PATENT DOCUMENTS

| | | |
|---|---|---|
| EP | 0705571 A1 | 4/1996 |
| EP | 0640317 B1 | 9/1999 |
| EP | 1532933 B1 | 5/2008 |
| EP | 1707143 B1 | 6/2008 |
| EP | 1943957 A2 | 7/2008 |
| EP | 1849424 B1 | 4/2009 |
| EP | 2042117 A1 | 4/2009 |
| EP | 2060238 A1 | 5/2009 |
| EP | 1810625 B1 | 8/2009 |
| EP | 2090238 A1 | 8/2009 |
| EP | 2092905 A1 | 8/2009 |
| EP | 1747761 B1 | 10/2009 |
| EP | 1769766 B1 | 2/2010 |
| EP | 2151204 A1 | 2/2010 |
| EP | 2153791 A1 | 2/2010 |
| EP | 2243439 A1 | 10/2010 |
| WO | WO 93/22973 A1 | 11/1993 |
| WO | WO 96/35382 A1 | 11/1996 |
| WO | WO 98/00069 A1 | 1/1998 |
| WO | WO 98/57588 A1 | 12/1998 |
| WO | WO 99/23960 A1 | 5/1999 |
| WO | WO 99/40861 A1 | 8/1999 |
| WO | WO 00/25691 A1 | 5/2000 |

(56) References Cited

FOREIGN PATENT DOCUMENTS

| | | |
|---|---|---|
| WO | WO 01/28444 A1 | 4/2001 |
| WO | WO 03/013374 A1 | 2/2003 |
| WO | WO 03/020339 A2 | 3/2003 |
| WO | WO 03/028541 A2 | 4/2003 |
| WO | WO 03/030708 A2 | 4/2003 |
| WO | WO 03/068046 A2 | 8/2003 |
| WO | WO 2004/011037 A2 | 2/2004 |
| WO | WO 2005/052959 A2 | 6/2005 |
| WO | WO 2006/021269 A1 | 3/2006 |
| WO | WO 2006/036706 A1 | 4/2006 |
| WO | WO 2006/055166 A2 | 5/2006 |
| WO | WO 2008/045348 A2 | 4/2008 |
| WO | WO 2008/099529 A1 | 8/2008 |
| WO | WO 2008/101356 A1 | 8/2008 |
| WO | WO 2009/022614 A1 | 2/2009 |
| WO | WO 2009/036818 A1 | 3/2009 |
| WO | WO 2009/059741 A1 | 5/2009 |
| WO | WO 2009/082477 A2 | 7/2009 |
| WO | WO 2010/104755 A1 | 9/2010 |
| WO | WO 2011/089717 A1 | 7/2011 |

OTHER PUBLICATIONS

Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).
Chen et al., "Heat-Induced Changes in the Mechanics of a Collagenous Tissue: Isothermal Free Shrinkage," Transactions of the ASME, vol. 119, pp. 372-378 (Nov. 1997).
Chen et al., "Heat-Induced Changes in the Mechanics of a Collagenous Tissue: Isothermal, Isotonic Shrinkage," Transactions of the ASME, vol. 120, pp. 382-388 (Jun. 1998).
Chen et al., "Heat-induced changes in the mechanics of a collagenous tissue: pseudoelastic behavior at 37° C," Journal of Biomechanics, 31, pp. 211-216 (1998).
Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=Ml&sp=1 . . . , accessed Aug. 25, 2009.
Henriques. F.C., "Studies in thermal injury V. The predictability and the significance of thermally induced rate processes leading to irreversible epidermal injury." Archives of Pathology, 434, pp. 489-502 (1947).
Hörmann et al., "Reversible and irreversible denaturation of collagen fibers." Biochemistry, 10, pp. 932-937 (1971).
Lee et al., "A multi-sample denaturation temperature tester for collagenous biomaterials," Med. Eng. Phy., vol. 17, No. 2, pp. 115-121 (Mar. 1995).
Moran et al., "Thermally Induced Shrinkage of Joint Capsule," Clinical Orthopaedics and Related Research, No. 281, pp. 248-255 (Dec. 2000).
Wall et al., "Thermal modification of collagen," J Shoulder Elbow Surg, No. 8, pp. 339-344 (Jul./Aug. 1999).
Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).
Wells et al., "Altered Mechanical Behavior of Epicardium Under Isothermal Biaxial Loading," Transactions of the ASME, Journal of Biomedical Engineering, vol. 126, pp. 492-497 (Aug. 2004).
Wright, et al., "Time-Temperature Equivalence of Heat-Induced Changes in Cells and Proteins," Feb. 1998. ASME Journal of Biomechanical Engineering, vol. 120, pp. 22-26.
Gibson, "Magnetic Refrigerator Successfully Tested," U.S. Department of Energy Research News, accessed online on Aug. 6, 2010 at http://www.eurekalert.org/features/doe/2001-11/dlmrs062802.php (Nov. 1, 2001).
Glaser and Subak-Sharpe, *Integrated Circuit Engineering*, Addison-Wesley Publishing, Reading, MA (1979). (book—not attached).
Kurt Gieck & Reiner Gieck, *Engineering Formulas* § Z.7 (7th ed. 1997).
National Semiconductors Temperature Sensor Handbook—http://www.national.com/appinfo/tempsensors/files/temphb.pdf; accessed online: Apr. 1, 2011.
U.S. Appl. No. 12/911,943, filed Oct. 26, 2010.
U.S. Appl. No. 12/963,001, filed Dec. 8, 2010.
U.S. Appl. No. 12/775,724, filed May 7, 2010.
U.S. Appl. No. 12/622,113, filed Nov. 19, 2009.
U.S. Appl. No. 12/635,415, filed Dec. 10, 2009.
U.S. Appl. No. 12/647,134, filed Dec. 24, 2009.
U.S. Appl. No. 13/221,410, filed Aug. 30, 2011.
International Search Report for PCT/US2012/046197, Oct. 1, 2012 (5 pages).

\* cited by examiner

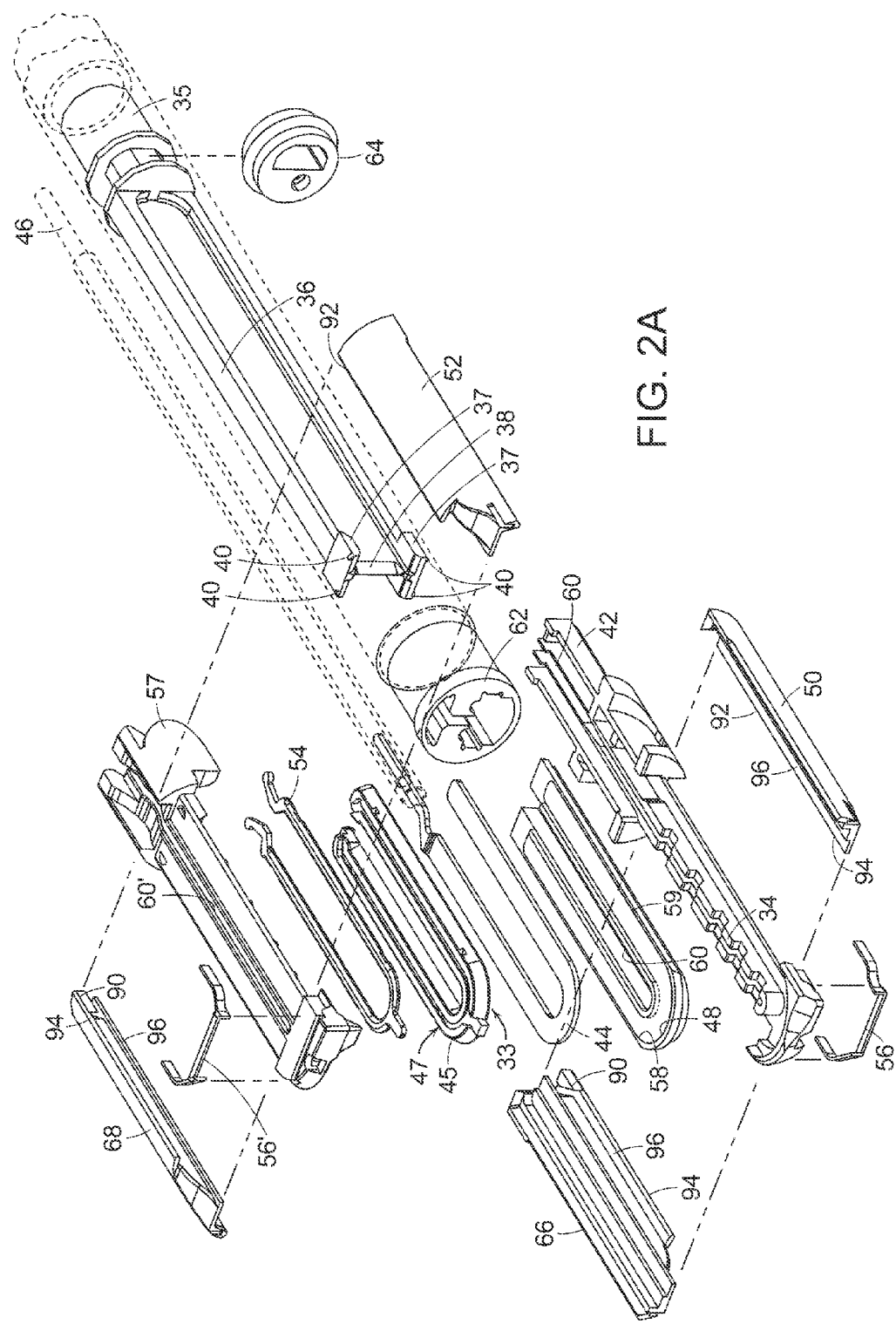

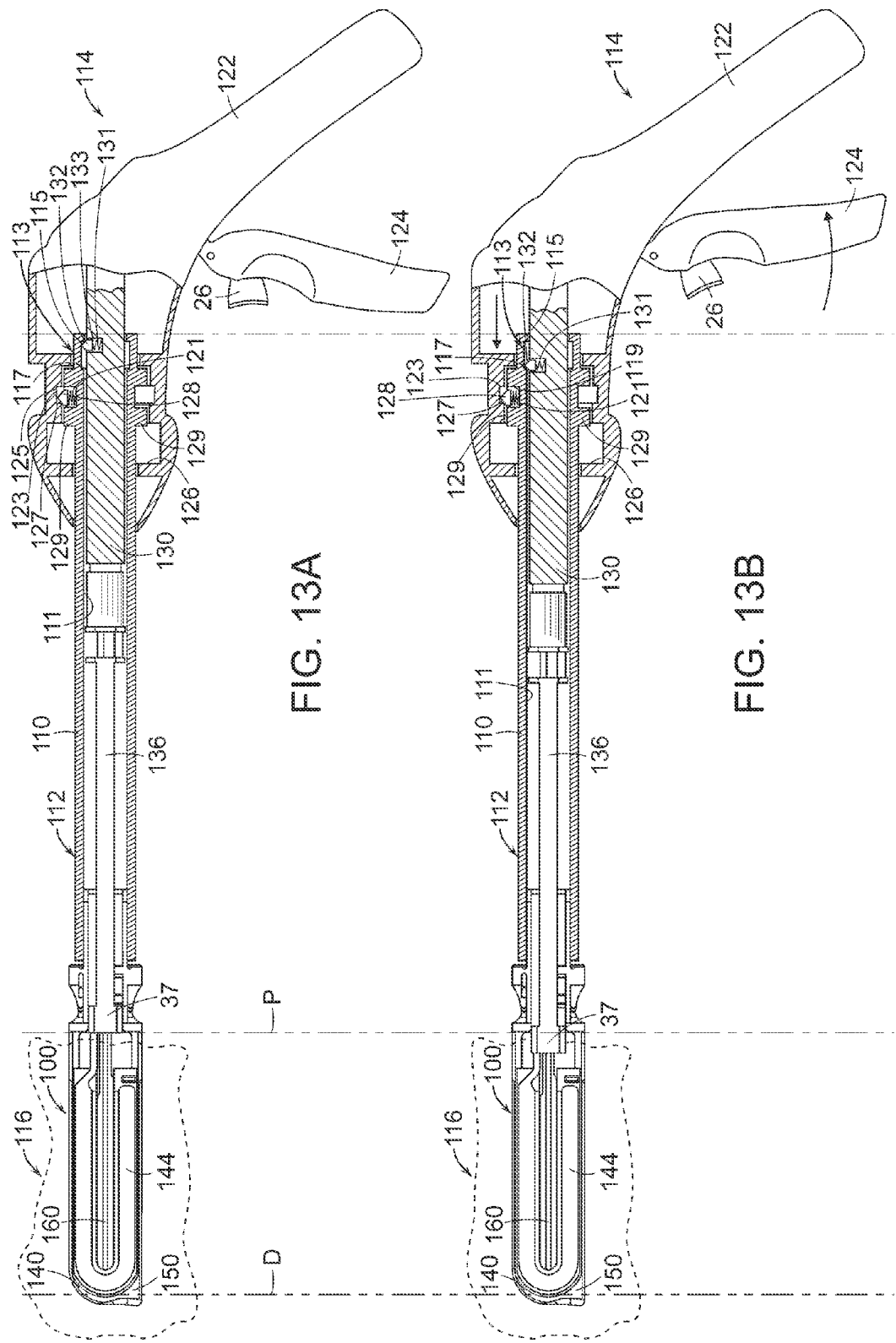

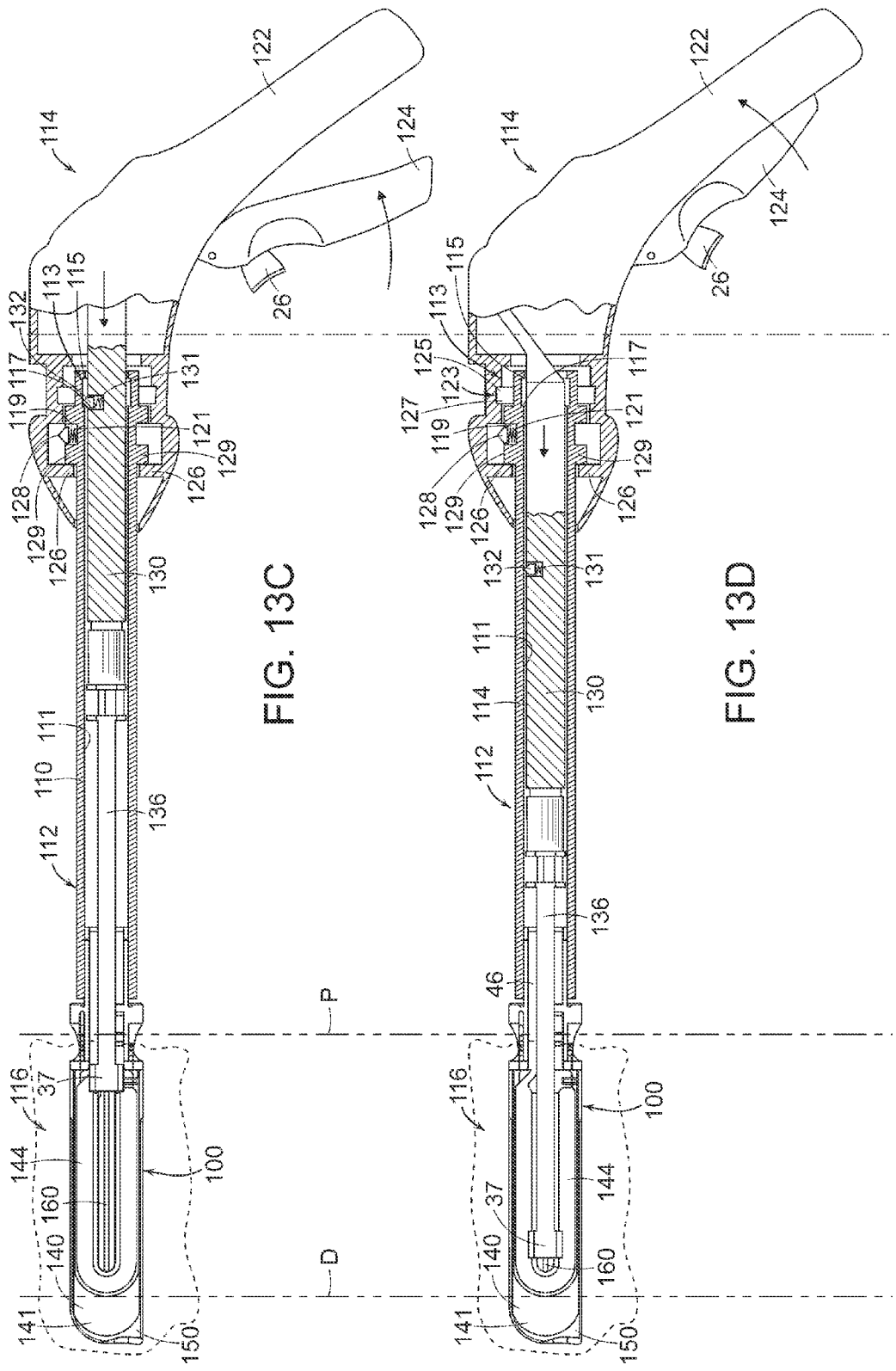

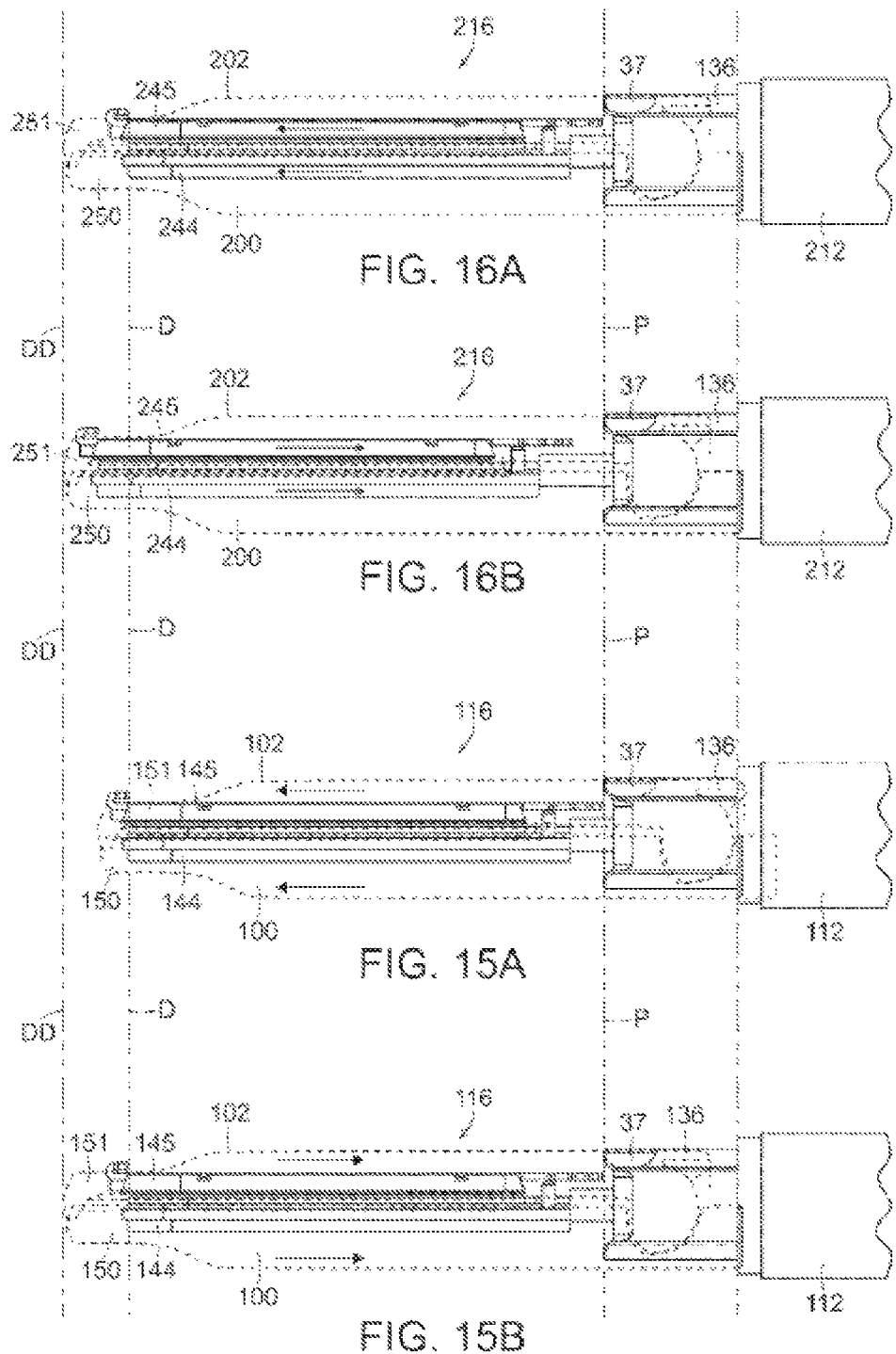

SURGICAL INSTRUMENTS FOR TENSIONING TISSUE

FIELD

The present disclosure relates generally to surgical instruments suitable for sealing tissue and, more particularly, relates to surgical instruments comprising an electrode and configured to tension tissue adjacent tissue being sealed by the electrode.

BACKGROUND

In various open, endoscopic, and/or laparoscopic surgeries, for example, it may be desirable to coagulate, seal, and/or fuse tissue. One method of sealing tissue relies upon the application of energy, such as electrical energy, for example, to tissue captured or clamped within an end-effector or an end-effector assembly of a surgical instrument in order to cause thermal effects within the tissue. Various mono-polar and bi-polar radio frequency (Rf) surgical instruments and surgical techniques have been developed for such purposes. In general, the delivery of Rf energy to the captured tissue can elevate the temperature of the tissue and, as a result, the energy can at least partially denature proteins within the tissue. Such proteins, such as collagen, for example, can be denatured into a proteinaceous amalgam that intermixes and fuses, or seals, together as the proteins renature. As the treated region heals over time, this biological seal may be reabsorbed by the body's wound healing process.

In certain arrangements of a bi-polar radiofrequency (Rf) surgical instrument, the surgical instrument can comprise opposing first and second jaws, wherein each jaw can comprise an electrode. In use, the tissue can be captured between the jaws such that energy can flow between the electrodes in the opposing jaws and through the tissue positioned therebetween. Such instruments may have to seal many types of tissues, such as anatomic structures having walls with irregular or thick fibrous content, bundles of disparate anatomic structures, substantially thick anatomic structures, and/or tissues with thick fascia layers such as large diameter blood vessels, for example. With particular regard to sealing large diameter blood vessels, for example, such applications may require a high strength tissue seal immediately post-treatment.

The foregoing discussion is intended only to illustrate various aspects of the related art and should not be taken as a disavowal of claim scope.

SUMMARY

In one non-limiting embodiment, the present disclosure, in part, is directed to an end-effector configured to be attached to a surgical instrument. The end-effector comprises a first jaw comprising an electrode and a second jaw. At least one of the first jaw and the second jaw is movable relative to the other jaw between an open position and a closed position. In the closed position, a first region of tissue positioned intermediate the first jaw and the second jaw is compressed. The first jaw comprises a first slider member movably attached to the first jaw and movable relative to the electrode. The first slider member comprises a first tissue-contacting surface configured to engage a second region of the tissue. The second jaw comprises a second slider member movably attached to the second jaw and movable relative to the electrode. The second slider member comprises a second tissue-contacting surface configured to engage the second region of the tissue. The first slider member and the second slider member are configured to apply a tensile force to tissue positioned intermediate the first region and the second region when the first slider member and the second slider member are moved relative to the electrode.

In one non-limiting embodiment, the present disclosure, in part, is directed to a surgical instrument comprising a first jaw comprising an electrode, a second jaw, and movement means for moving at least one of the first jaw and the second jaw relative to the other jaw between an open position and a closed position to compress a first region of tissue positioned intermediate the first jaw and the second jaw. The first jaw comprises a first member movably attached to the first jaw and movable relative to the electrode. The first member comprises a first tissue-contacting surface configured to grip a second region of the tissue. The second jaw comprises a second member movably attached to the second jaw and movable relative to the electrode. The second member comprises a second tissue-contacting surface configured to grip the second region of the tissue. The surgical instrument comprises biasing means for biasing at least the first member relative to the electrode to tension the tissue positioned intermediate the first region and the second region.

In one non-limiting embodiment, the present disclosure, in part, is directed to a surgical instrument, comprising an elongate shaft comprising a proximal end and a distal end, a handle portion extending from the proximal end of the elongate shaft, and an end-effector extending from the distal end of the elongate shaft. The end-effector comprises a first jaw comprising an electrode and a second jaw. At least one of the first jaw and the second jaw is movable relative to the other jaw between an open position and a closed position. In the closed position, a first region of tissue positioned intermediate the first jaw and the second jaw is compressed. The first jaw comprises a first slider member movably attached to the first jaw and movable relative to the electrode. The first slider member comprises a first tissue-contacting surface configured to engage a second region of the tissue. The second jaw comprises a second slider member movably attached to the second jaw and movable relative to the electrode. The second slider member comprises a second tissue-contacting surface configured to engage the second region of the tissue. The first slider member and the second slider member are configured to apply a tensile force to tissue positioned intermediate the first region and the second region when the first slider member and the second slider member are moved relative to the electrode.

BRIEF DESCRIPTION OF THE DRAWINGS

Various features of the embodiments described herein are set forth with particularity in the appended claims. The various embodiments, however, both as to organization and methods of operation, together with the advantages thereof, may be understood in accordance with the following description taken in conjunction with the accompanying drawings as follows.

FIG. 2A is an exploded perspective view of the end-effector of FIG. 2 in accordance with at least one non-limiting embodiment of the present disclosure;

FIGS. 13A-13D illustrate the operation of a surgical instrument in accordance with at least one non-limiting embodiment of the present disclosure;

FIGS. 15A-15B illustrate the movement of portions of the end-effector of FIGS. 13A-13D;

FIGS. 16A-16B illustrate the movement of portions of the end-effector of FIGS. 11 and 12.

Figure 1:
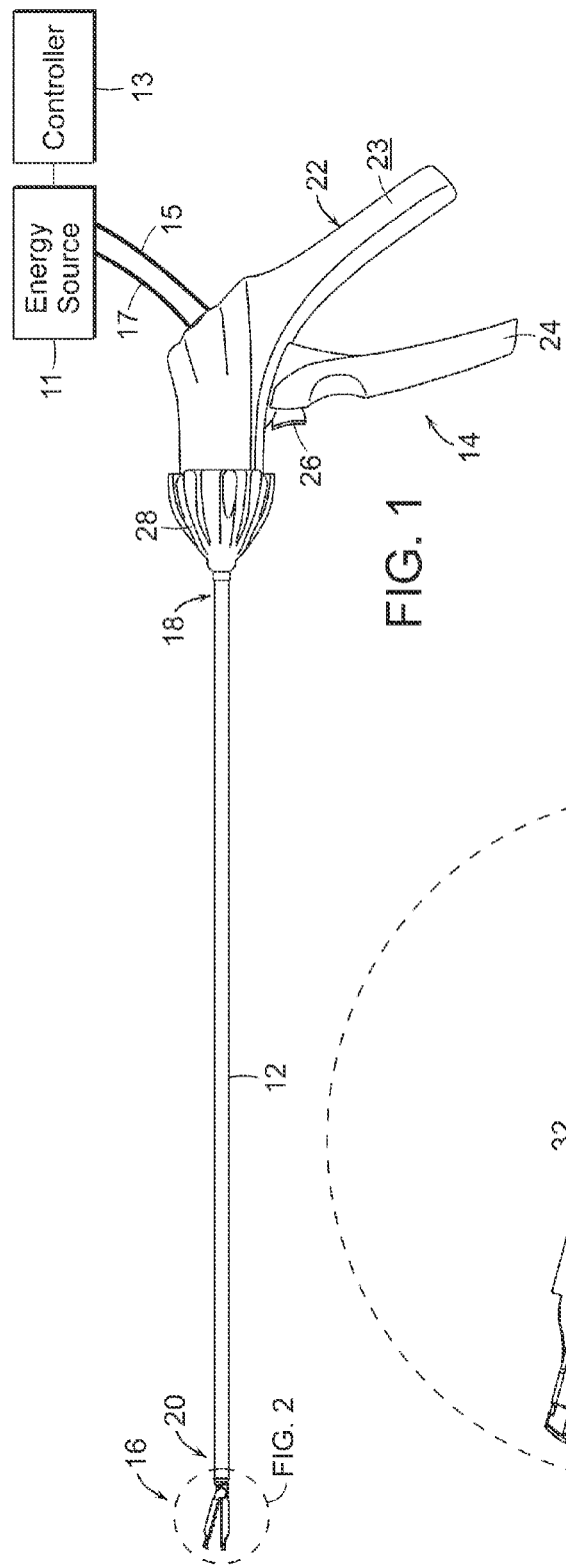
FIG. 1 is a side view of a surgical instrument in accordance with at least one non-limiting embodiment of the present disclosure.

Corresponding reference characters indicate corresponding parts throughout the several views. The example embodiments set out herein illustrate various embodiments of the present disclosure, in one form, and such example embodiments are not to be construed as limiting the scope of the present disclosure in any manner.

DETAILED DESCRIPTION

Various embodiments are directed to apparatuses, systems, and methods for the treatment of tissue. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and illustrative. Variations and changes thereto may be made without departing from the scope of the claims.

Reference throughout the specification to "various embodiments," "some embodiments," "one embodiment," "certain embodiments," or "in an embodiment", or the like, means that a particular feature, structure, or characteristic described in connection with the embodiment is included in at least one embodiment. Thus, appearances of the phrases "in various embodiments," "in some embodiments," "in one embodiment," "in certain embodiments," or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation.

The entire disclosures of the following non-provisional United States patents are hereby incorporated by reference herein:

U.S. Pat. No. 7,381,209, entitled ELECTROSURGICAL INSTRUMENT;

U.S. Pat. No. 7,354,440, entitled ELECTROSURGICAL INSTRUMENT AND METHOD OF USE;

U.S. Pat. No. 7,311,709, entitled ELECTROSURGICAL INSTRUMENT AND METHOD OF USE;

U.S. Pat. No. 7,309,849, entitled POLYMER COMPOSITIONS EXHIBITING A PTC PROPERTY AND METHODS OF FABRICATION;

U.S. Pat. No. 7,220,951, entitled SURGICAL SEALING SURFACES AND METHODS OF USE;

U.S. Pat. No. 7,189,233, entitled ELECTROSURGICAL INSTRUMENT;

U.S. Pat. No. 7,186,253, entitled ELECTROSURGICAL JAW STRUCTURE FOR CONTROLLED ENERGY DELIVERY;

U.S. Pat. No. 7,169,146, entitled ELECTROSURGICAL PROBE AND METHOD OF USE;

U.S. Pat. No. 7,125,409, entitled ELECTROSURGICAL WORKING END FOR CONTROLLED ENERGY DELIVERY; and U.S. Pat. No. 7,112,201, entitled ELECTROSURGICAL INSTRUMENT AND METHOD OF USE.

Various embodiments of systems and methods of the present disclosure relate to creating thermal "welds", "seals" and/or "fusion" within native tissue volumes, which are indicated in the figures as "Ti". These terms may be used interchangeably herein to describe thermal treatments of a targeted tissue volume that can result in a substantially uniform fused-together tissue mass, for example, in welding blood vessels that exhibit substantial burst strength immediately post-treatment. The strength of such welds is particularly useful for (i) permanently sealing blood vessels in vessel transection procedures; (ii) welding organ margins in resection procedures; (iii) welding other anatomic ducts wherein permanent closure is required; and also (iv) for performing vessel anastomosis, vessel closure, and/or other procedures that join together anatomic structures or portions thereof. The sealing, welding, and/or fusion of tissue as disclosed herein is to be distinguished from "coagulation", "hemostasis" and other similar descriptive terms that generally relate to the collapse and occlusion of blood flow within small blood vessels or vascularized tissue. For example, any surface application of thermal energy can cause coagulation or hemostasis—but does not fall into the category of "sealing" as the term is used herein. Such surface coagulation may not create a seal that provides any substantial strength in the treated tissue.

At the molecular level, the phenomena of truly "sealing" tissue as disclosed herein may result from the thermally-induced denaturation of collagen and/or other protein molecules in a targeted tissue volume to create a transient liquid or gel-like proteinaceous amalgam. In various circumstances, a selected energy density can be provided in the targeted tissue to cause hydrothermal breakdown of intra- and inter-molecular hydrogen crosslinks in the collagen and/or other protein molecules. The denatured amalgam can be maintained at a selected level of hydration—without desiccation—for a selected time interval which can be very brief. In various embodiments, the targeted tissue volume can be maintained under a selected high level of mechanical compression to insure that the unwound strands of the denatured proteins are in close proximity to one another to allow their re-intertwining and re-entanglement. Upon the thermal relaxation, or cooling, of the tissue, the intermixed amalgam can result in protein entanglement as re-crosslinking or renaturation occurs to thereby cause a uniform fused-together mass.

Further to the above, the thermally-induced denaturation of collagen and/or other protein molecules described above can, in various circumstances, result in permanent changes to the tissue. In certain circumstances, the tissue can be heated in a manner which allows the collagen molecules to permanently unwind and damage the tissue. In at least some such circumstances, the amount of damage done to the tissue can be measured by the amount in which the tissue shrinks as a result of the thermal energy applied thereto. For example, greatly-damaged tissue may tend to shrink more than lesser-damaged tissue. Such concepts are discussed in greater detail in *Continuum thermodynamics and the clinical treatment of disease and injury*, J. D. Humphrey, Appl. Mech. Rev., vol. 56, no. 2, March 2003; *Heat-induced changes in the mechanics of a collagenous tissue: Isothermal isotonic-shrinkage*, Chen, S. S., Wright, N. T., Humphrey, J. D., ASME Journal of Biomechanical Engineering 120, 382-388, 1998; and *Kinetics of thermal damage to a collagenous membrane under biaxial isotonic loading*, Harris, J. L., Humphrey J. D., IEEE Trans. Biomed. Eng. 2004 February, 51(2): 371-9, the entire disclosures of which are incorporated by reference herein.

In various circumstances, the amount in which the tissue can be damaged by the application of thermal energy thereto can be predicted. More particularly, the denaturation of the collagen within the tissue can be a function of at least two variables such as, one, the temperature to which the tissue is heated and, two, the time in which the tissue is heated, for example. Stated another way, the denaturation of the collagen within the tissue can be a function of time and temperature. It is believed by the Applicants that the degree to which the collagen is denaturized can also be a function of another variable, i.e., the mechanical force applied to the tissue. More particularly, it is believed by the Applicants that when a tensile load is applied to the tissue at the same time that the tissue is being exposed to thermal energy, excessive denaturation of the collagen can be reduced, delayed, and/or possibly prevented. It is believed that the tensioning of the tissue inhibits an undesired amount of unwinding and/or shortening of the collagen molecules. Thus, in various circumstances, the damage to tissue can be reduced and/or avoided when the tissue is stretched, for example.

Various embodiments disclosed herein provide electrosurgical jaw structures adapted for transecting captured tissue between the jaws and for contemporaneously sealing the captured tissue margins with controlled application of RF energy or other energy. The jaw structures can comprise a scoring element which can cut or score tissue independently of the tissue capturing and sealing functions of the jaw structures. The jaw structures can comprise first and second opposing jaws that carry fuses, such as positive temperature coefficient materials ("PTC" materials), for example, for modulating energy delivery to the engaged tissue.

The embodiments of the devices described herein may be introduced inside a patient using minimally invasive or open surgical techniques under direct control of a clinician or by way of indirect control of a clinician through the use of robot assistance. In some instances, it may be advantageous to introduce the devices inside the patient using a combination of minimally invasive and open surgical techniques. Minimally invasive techniques may provide more accurate and effective access to the treatment region for diagnostic and treatment procedures and include but are not limited to numerous laparoscopic approaches including the use of multiple trocars or ports distributed about the patient, multiple trocars placed at a single site, and/or a single trocar with multiple ports placed in a location such as, but not limited to, the umbilicus, for example. To reach internal treatment regions within the patient, the devices described herein may be inserted through natural openings of the body such as the mouth, anus, and/or vagina, for example. Minimally invasive procedures performed by the introduction of various medical devices into the patient through a natural opening of the patient are known as Natural Orifice, Transluminal, Endoscopic Surgery or NOTES™ procedures. Some portions of the devices may be introduced to the tissue treatment region percutaneously or through small—keyhole—incisions.

Endoscopic minimally invasive surgical and diagnostic medical procedures can be used to evaluate and treat internal organs by inserting a small tube into the body. The endoscope may have a rigid or a flexible tube. A flexible endoscope may be introduced either through a natural body opening (e.g., mouth, anus, and/or vagina) or via a trocar through a relatively small—keyhole—incision (usually 0.5-1.5 cm). The endoscope can be used to observe surface conditions of internal organs, including abnormal or diseased tissue such as lesions and other surface conditions and capture images for visual inspection and photography. The endoscope may be adapted and configured with working channels for introducing medical instruments to the treatment region for taking biopsies, retrieving foreign objects, and/or performing surgical procedures.

Certain example embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting example embodiments and that the scope of the various embodiments of the present disclosure is defined solely by the claims. The features illustrated or described in connection with one example embodiment may be combined with the features of other embodiments. Such modifications and variations are intended to be included within the scope of the present disclosure.

In various embodiments, referring to FIG. 1, a surgical instrument 10 can comprise an elongate shaft 12, a handle portion 14, and an end-effector 16. The end-effector 16 can comprise a proximal end configured to be engaged with the shaft 12, a distal end positioned distal from the shaft 12, and a longitudinal axis defined intermediate the proximal end and the distal end. The elongate shaft 12 can comprise a proximal end 18 and a distal end 20. The handle portion 14 can extend from the proximal end 18 of the elongate shaft 12 and the end-effector 16 can extend from the distal end 20 of the elongate shaft 12. The terms "proximal" and "distal" are used herein with reference to the clinician or surgeon (hereafter "surgeon") holding the handle portion 14 of the surgical instrument 10. For example, the end-effector 16 is located distal from the surgeon while the handle portion 14 is located proximal to the surgeon. In various embodiments, the handle portion 14 can comprise two portions which are assembled together to form the handle portion 14, for example. In one embodiment, the two portions of the handle portion 14 can be snap-fit, press-fit, adhered, glued, and/or otherwise fastened to one another.

In one embodiment, the surgical instrument 10 and portions of the end-effector 16 can be in communication with an energy source 11 through conductors 15 and 17 such that the jaws or other portions of the end-effector 16 can function as a pair of bi-polar electrodes, for example, wherein one electrode can have a positive polarity (+) and one electrode can have a negative polarity (−), as is discussed in greater detail herein. In one embodiment, the conductor 15 can have a positive polarity and the conductor 17 can have a negative polarity, for example. The conductors 15 and 17 can be in electrical communication with the end-effector 16 and/or other portions of the surgical instrument 10 such that energy can be supplied from the energy source 11 to the end-effector 16 or other portions of the surgical instrument 10 through the conductors 15 and 17. In one embodiment, the energy source 11 can be configured to supply energy, such as electrical energy, RF energy, ultrasonic energy, and/or thermal energy, for example, from the energy source 11 to the tissue compressed within the end-effector 16 to seal or otherwise energize the tissue. The delivery of the energy from the energy source 11, such as the magnitude, duration, wave form, and/or frequency, for example, of the energy can be sufficiently controlled or modulated by a controller 13 to provide a desired amount or type of energy to the surgical instrument 10. Although not shown, it is conceived that the energy source, controller, and/or conductors may be located on and/or within the device (e.g., within handle portion 14). Various suitable energy sources and controllers are known to those of skill in the art.

In one embodiment, the handle portion 14 can comprise a grip 22 including a gripping surface 23, a trigger 24, and an actuation button 26 optionally positioned on and/or extending from the trigger 24. In various embodiments, the actuation button 26 can be configured as a separate trigger. In other various embodiments, the actuation button can be positioned on the handle portion 14, instead of the trigger 24, for example. In use, as described in greater detail below, the trigger 24 can be moved or pivoted proximally toward the grip 22 to actuate and/or close the end-effector 16 of the surgical instrument 10. In one embodiment, the handle portion 14 can comprise a rotatable knob 28 operably engaged with and/or attached to the proximal end 18 of the elongate shaft 12. In at least one such embodiment, the elongate shaft 12 can form a longitudinal axis extending between the proximal end 18 and the distal end 20 of the shaft 12 wherein the rotatable knob 28 can allow a surgeon to rotate the end-effector 16 about the longitudinal axis in the direction indicated by arrow "R" (FIG. 5), for example, in order to better position the end-effector 16 for various surgical procedures. In other embodiments, the end-effector 16 may not be rotatable relative to the handle portion 14. In one embodiment, the end-effector 16 can be articulated relative the elongate shaft 12 in any suitable manner for various surgical procedures.

Figure 2:
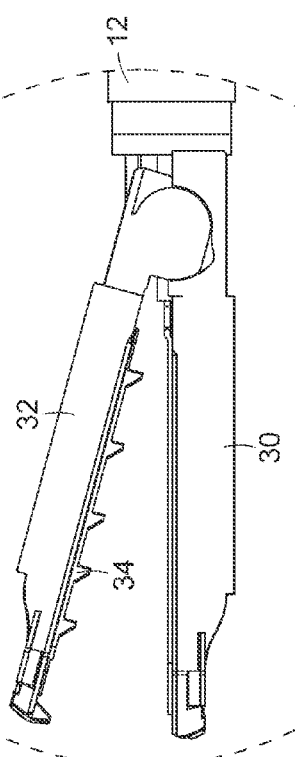
FIG. 2 is an enlarged side view of an end-effector of the surgical instrument of FIG. 1 in accordance with at least one non-limiting embodiment of the present disclosure.
Figure 3:
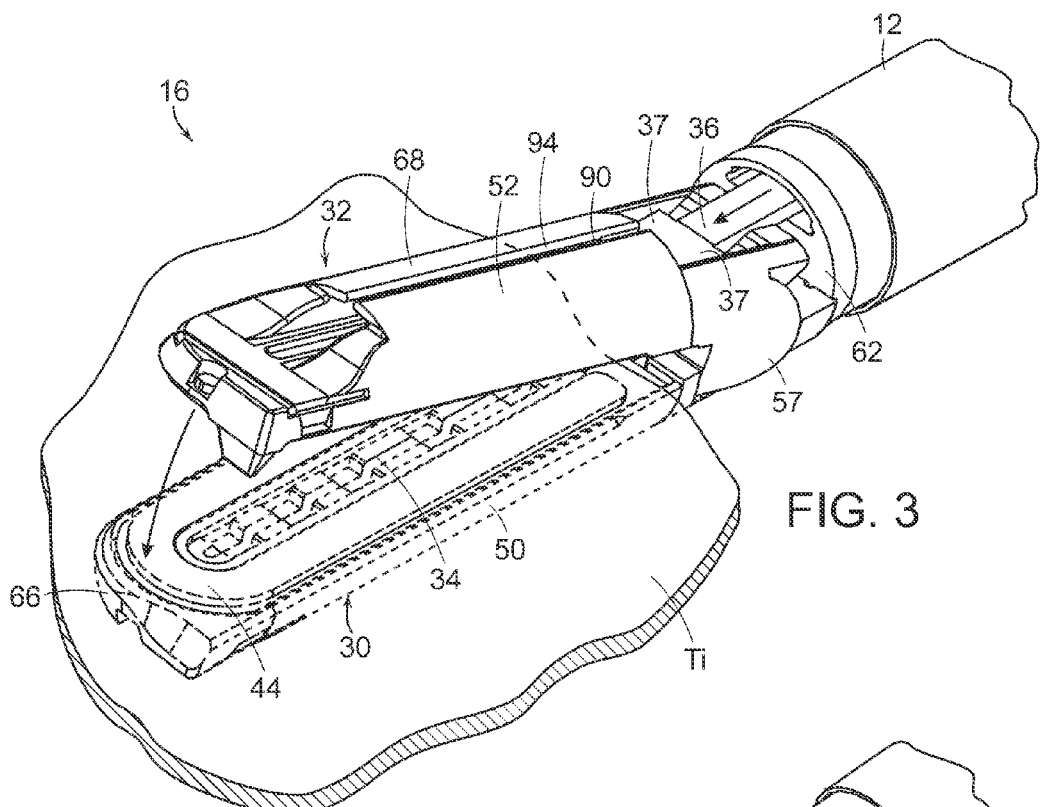
FIGS. 3, 3A, and 4 are perspective views of an end-effector of a surgical instrument engaging tissue in accordance with at least one non-limiting embodiment of the present disclosure.
Figure 3A:
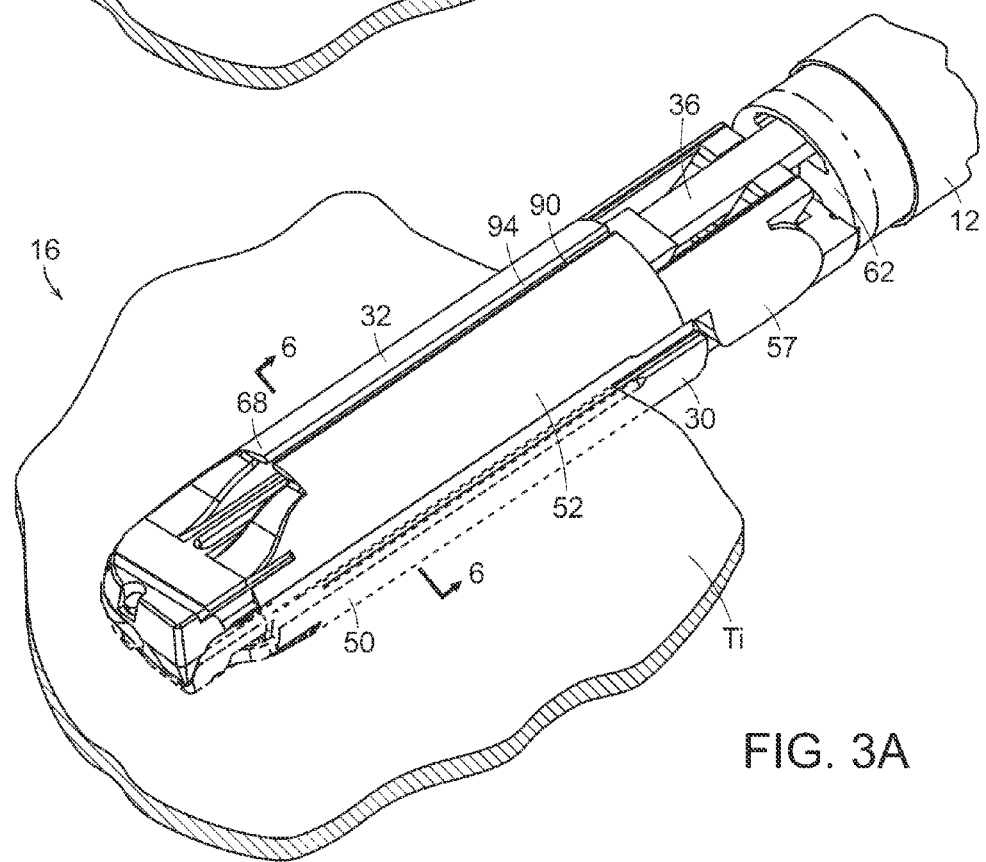
Figure 4:
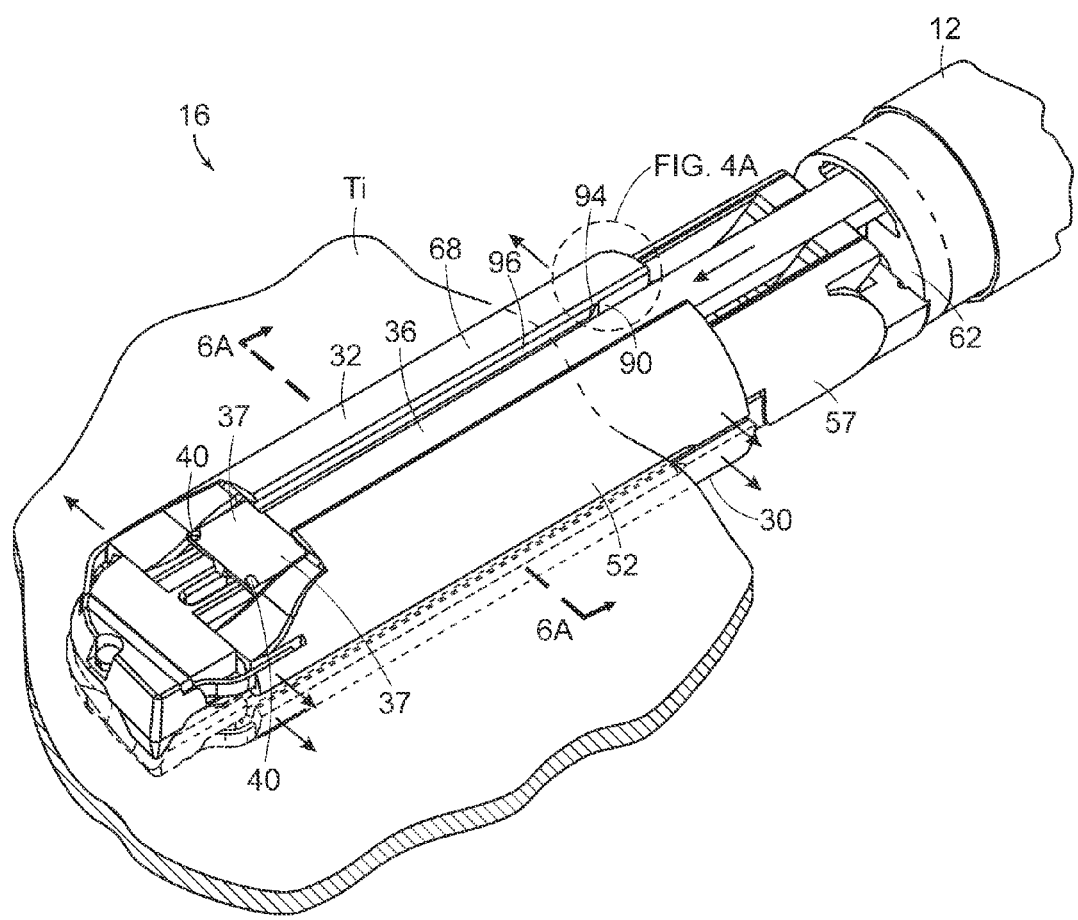
Figure 4A:
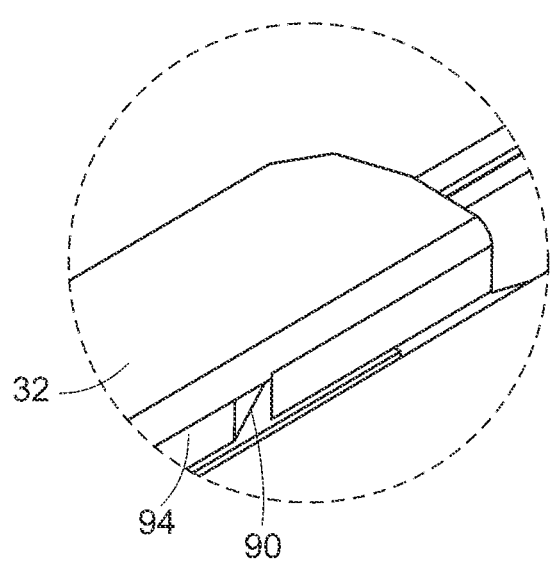
FIG. 4A is a detail view of the indicated portion of FIG. 4 in accordance with one non-limiting embodiment of the present disclosure.
Figure 5:
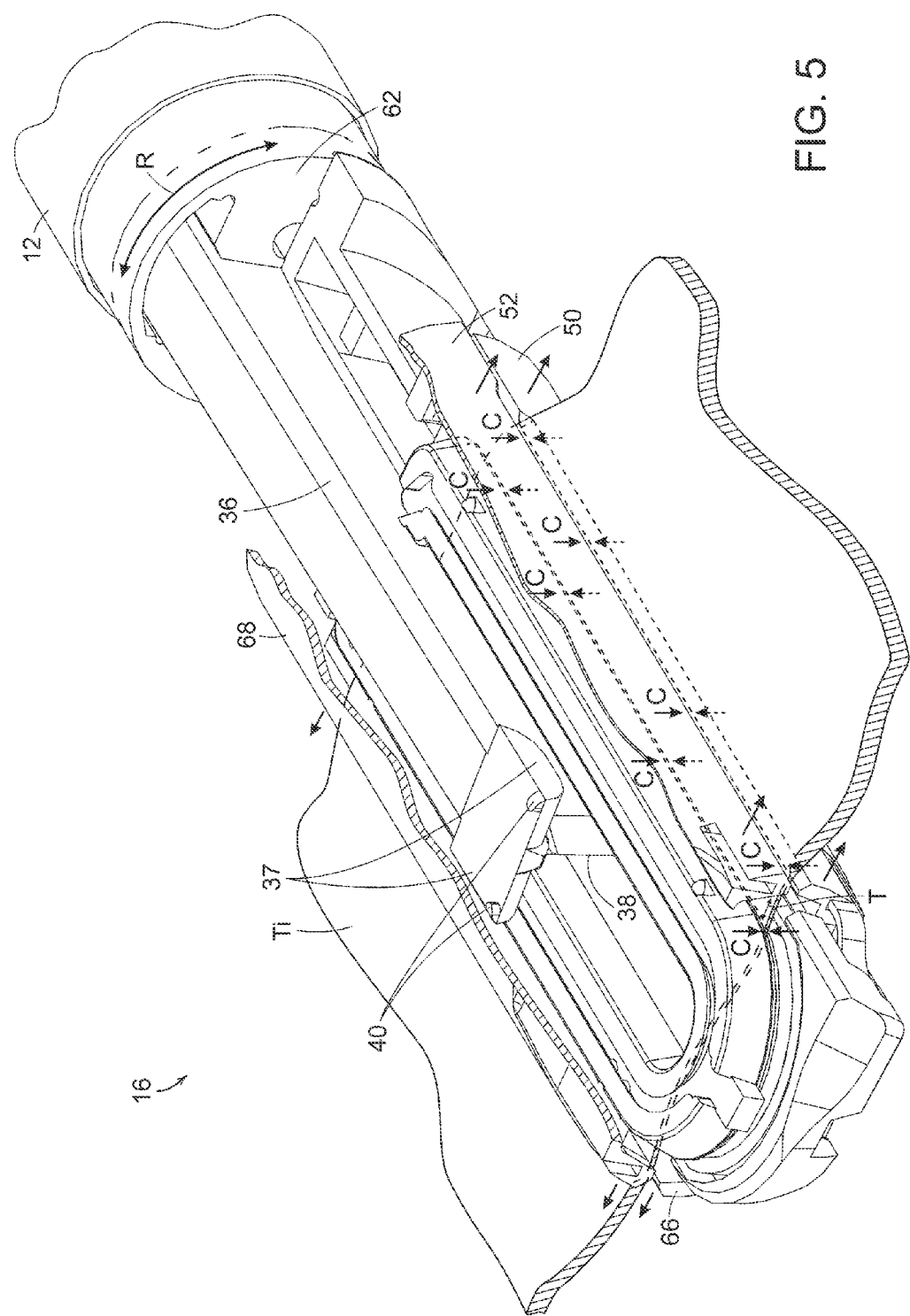
FIG. 5 is partial cut-away perspective view of an end-effector of a surgical instrument engaging tissue in accordance with at least one non-limiting embodiment of the present disclosure.

In one embodiment, referring to FIGS. 1, 2, and 2A, the end-effector 16 can comprise a first jaw 30 and a second jaw 32. In various embodiments, the first jaw 30 can comprise an electrode 44 and the second jaw 32 can comprise an electrode 45 and/or a fuse 33, which can be comprised of a PTC material, for example, as discussed below. In various embodiments, at least one of the first jaw 30 and the second jaw 32 can be configured to move relative to the other jaw between an open position and a closed position upon the actuation of the trigger 24. In one embodiment, the open position of the end effector 16 is illustrated in FIGS. 1, 2, and 3 and the closed position of the end effector 16 is illustrated in FIGS. 3A, 4, and 5. In various embodiments, only one of the first jaw 30 and the second jaw 32 may be movable relative to the other jaw while, in other embodiments, the first jaw 30 and the second jaw 32 may both be movable relative to each other. In either event, the end-effector 16 can engage and compress tissue, or layers of tissue, therewithin when the second jaw 32 is moved from an open position into a closed position, for example. Such movement of the second jaw 32 can help to uniformly, or substantially uniformly, compress the tissue and reduce the amount of fluids, such as water or blood, for example, contained within the tissue in the area of compressed tissue. In various embodiments, one or both of the first jaw 30 and the second jaw 32 can comprise a tissue-gripping portion, or teeth, 34 configured to aid the first jaw 30 and the second jaw 32 in holding tissue or layers of tissue within the end-effector 16 during the closure of the end-effector 16 and/or the cutting and sealing of the tissue, as described below.

In one embodiment, referring to FIGS. 1-4, the trigger 24 can advance a movable member 36 distally within the end-effector 16 when the trigger 24 is moved proximally toward the grip 22. In various embodiments, a conduit, bar, or tube 35 can be operably engaged with the trigger 24 wherein the tube 35 can extend from the handle portion 14 to the proximal end of the end-effector 16 and/or the distal end 20 of the elongate shaft 12. The tube 35 can be operably engaged with the movable member 36 and can be used to move the movable member 36 distally and/or proximally within the end-effector 16 and/or the elongate shaft 12. The actuation mechanisms within the handle portion 14 that can move the tube 35 within the elongate shaft 12 and the movable member 36 within the end-effector 16 upon the actuation of the trigger 24 are described in greater detail in co-pending U.S. patent application Ser. No. 12/732,992, entitled SURGICAL CUTTING AND SEALING INSTRUMENT WITH REDUCED FIRING FORCE, filed on Mar. 26, 2010, the disclosure of which is incorporated by reference herein in its entirety. In one embodiment, the movable member 36 can comprise an I-beam or E-beam configuration and can comprise one or more fins 37 extending therefrom configured to engage the first jaw 30 and the second jaw 32 and move, or pivot, the first and second jaws 30 and 32 into the closed position when the movable member 36 is advanced distally within the end-effector 16. In one embodiment, the progression of the movable member 36 and the closure of the first and second jaws 30 and 32 is illustrated in FIGS. 3 and 3A. In one embodiment, such a closure mechanism can provide substantially equal tissue compression in tissue of substantially the same thickness. In various embodiments, referring primarily to FIG. 2A, the movable member 36 can comprise or can be attached to a cutting member, or knife edge, 38 configured to cut tissue positioned within the end-effector 16. The movable member 36 can also comprise one or more cams or camming surfaces 40 positioned proximate to the distal end thereof which are configured to bias portions of the first jaw 30 and the second jaw 32 laterally, as described in further detail herein.

In one embodiment, referring to FIGS. 2A-4, 5, 6, and 6A, the first jaw 30 can comprise a base 42 including a gripping portion 34 configured to grip tissue, an electrode 44 in electrical communication with a conductive element 46, a support member 48 configured to support the electrode 44, a first slider member 50, a third slider member 66, and a biasing member, or spring element, 56. The conductive element 46 can extend into the elongate shaft 12 and can be in electrical communication with the conductor 15, for example, such that current can flow between the electrode 44 and the conductor 15 during use. In certain embodiments, the electrode 44 can be press-fit, snap fit, and/or otherwise engaged within a channel 58 (FIG. 2A) of the support member 48 wherein, in at least one embodiment, relative movement between the electrode 44 and the support member 48 can be prevented, or at least limited. In various embodiments, a first end of the electrode 44 can be positioned proximate to the distal end 20 of the elongate shaft 12 and a second end of the electrode 44 can be positioned distally with respect to the distal end 20 of the elongate shaft 12. In at least one such embodiment, an axis can be defined between the first end of the electrode 44 and the second end of the electrode 44. In certain embodiments, the electrode 44 can comprise a U-shaped configuration, for example. In various embodiments, the first jaw 30 can comprise more than one electrode. Regardless of the shape and/or quantity of electrodes engaged with the support member 48, for example, the support member 48, and the electrodes attached thereto, can be snap-fit, press-fit, and/or otherwise engaged with the base 42. In one embodiment, a tissue-contacting surface 59 on the support member 48 can be comprised of an insulative and/or non-conductive material that can surround the electrode 44 such that energy supplied to the electrode 44, or at least a substantial portion of the energy supplied to the electrode 44, may flow from the electrode 44 to the second jaw 32. Other suitable portions of the first jaw 30 can be comprised of insulative and/or non-conductive materials as well such that a desired flow of energy through the end-effector 16 can be achieved.

In various embodiments, further to the above, the first slider member 50 and the third slider member 66 can be slidably attached to the base 42 of the first jaw 30. In at least one embodiment, the biasing member 56 can connect the distal end of the first slider member 50 and the distal end of the third slider member 66 to the distal end of the base 42. In at least one such embodiment, the biasing member 56 can comprise a base portion which is embedded within and/or otherwise attached to the base 42 and, in addition, two ends extending therefrom wherein one of the ends can be engaged with the first slider member 50 and the other end can be engaged with the second slider member 66. In various embodiments, the biasing member 56 can be configured to resiliently bias the first and third slider members 50 and 66 inwardly toward a longitudinal axis, or center, of the end-effector 16. In order to move the first and third slider members 50 and 66 outwardly, as described in greater detail below, the movable member 36 can engage the first and third slider members 50 and 66 and displace them outwardly. In at least one such embodiment, the cams 40 extending from the movable member 36 can engage the proximal ends of the first and third slider members 50 and 66 to displace the slider members 50 and 66 outwardly away from the longitudinal axis when the movable member 36 is advanced into the end effector 16. In use, the fins 37 of the movable member 36 can engage the second jaw 32 and pivot the second jaw 32 into a closed position prior to the cams 40 contacting the slider members 50 and 66. In at least one such embodiment, as a result, the slider members 50 and 66 would be moved outwardly after the second jaw 32 has been closed. In such embodiments, at least a portion of the fins 37 can lead, or be positioned distally, with respect to the cams 40. In certain embodiments, the fins 37 can engage the jaw 32 at the same time that the cams 40 contact the slider members 50 and 66. In at least one such embodiment, as a result, the slider members 50 and 66 would be moved outwardly at the same time that the second jaw 32 is closed. In either event, the first and third slider members 50 and 66 can be configured to be moved relative to and/or away from the electrode 44, relative to and/or away from a longitudinal axis of the end-effector 16, and/or relative to and/or away from the base 42.

In various embodiments, the base 42 of the first jaw 30 can comprise at least one first guide rail configured to guide the first slider member 50 along a predetermined path. In at least one such embodiment, the first slider member 50 can comprise at least one first channel or guide slot configured to slidably receive the first guide rail therein. In use, the first guide rail and the first guide slot can co-operate to limit the movement of the first slider member 50 such that the first slider member 50 moves laterally when it is displaced. Further to the above, the base 42 of the first jaw 30 can further comprise at least one third guide rail configured to guide the third slider member 66 along a predetermined path. In at least one such embodiment, the third slider member 66 can comprise at least one first channel or guide slot configured to slidably receive the first guide rail therein. In use, the third guide rail and the third guide slot can co-operate to limit the movement of the third slider member 66 such that the third slider member 66 moves laterally when it is displaced.

In various embodiments, as described above, the movable member 36 can comprise a cutting member, or knife edge, 38, for example, which can transect the tissue captured between the first jaw 30 and the second jaw 32 as the movable member 36 is advanced through the end-effector 16. In certain embodiments, further to the above, the knife edge 38 can lag the front, or leading, edge of the fins 37 such that the knife edge 38 may not contact the tissue until the second jaw 32 is in its closed position. In at least one such embodiment, the knife edge 38 may also lag the cams 40 such that the knife edge 38 may not contact the tissue until the slider members 50 and 66 have been displaced laterally. In certain embodiments, a surgical instrument can comprise a cutting member which is movable independently of the movable member 36. In at least one such embodiment, the movable member 36 can comprise fins 37 and cams 40, for example, which can close the second jaw 32 and displace the slider members 50 and 66, respectively, wherein a separate cutting member can be advanced distally at any suitable point during the operation of the instrument. In various embodiments, the surgical instrument can comprise a lock which can be configured to prevent the distal motion of the cutting member until the slider members 50 and 66 have been displaced laterally, for example. Regardless of when the cutting member is advanced to transect the tissue, in various embodiments, the first jaw 30 can also comprise a cutting member slot 60 configured to receive a portion of the cutting member 38 therein.

In one embodiment, referring now to FIGS. 2A-4, 5, 6, and 6A, the second jaw 32 can comprise a carrying member, or frame, 47, the fuse 33, which can be comprised of a PTC material, the electrode 45, a second slider member 52, a fourth slider member 68, a retaining clip 54, a biasing member, or spring element, 56', and a support portion 57. In various embodiments, the electrode 45 can be mounted to the carrying member 47 and the retaining clip 54 can be used to attach the carrying member 47 and the electrode 45 to the support portion 57 of the second jaw 32. Similar to the above, the second slider member 52 and the fourth slider member 68 can be slidably attached to the support portion 57. In at least one embodiment, the biasing member 56' can comprise a base portion mounted to the support portion 57 of the second jaw 32 and two ends extending from the base portion. A first end of the biasing member 56' can be engaged with the second slider member 52 and a second end of the biasing member 56' can be engaged with the fourth slider member 68 wherein the biasing member 56' can be configured to bias the second and fourth slider members 52 and 68 inwardly toward the longitudinal axis, or center, of the end-effector 16 and/or toward a longitudinal axis of the electrode 45. In use, similar to the above, the cams 40 extending from the movable member 36 can engage the proximal ends of the second and fourth slider members 52 and 68 and displace the second and fourth slider members 52 and 68 outwardly. In various embodiments, the second and fourth slider members 52 and 68 can be configured to be moved relative to and/or away from the electrode 45, relative to and/or away from the longitudinal axis of the end-effector 16, and/or relative to and/or away from the support portion 57. Similar to the above, the second jaw 32 can also comprise a cutting member slot 60' configured to receive a portion of the cutting member 38.

In various embodiments, the support portion 57 of the second jaw 32 can comprise at least one second guide rail configured to guide the second slider member 52 along a predetermined path. In at least one such embodiment, the second slider member 52 can comprise at least one second channel or guide slot configured to slidably receive the second guide rail therein. In use, the second guide rail and the second guide slot can co-operate to limit the movement of the second slider member 52 such that the second slider member 52 moves laterally when it is displaced. Further to the above, the support portion 57 of the second jaw 32 can further comprise at least one fourth guide rail configured to guide the fourth slider member 68 along a predetermined path. In at least one such embodiment, the fourth slider member 68 can comprise at least one fourth channel or guide slot configured to slidably receive the fourth guide rail therein. In use, the fourth guide rail and the fourth guide slot can co-operate to limit the movement of the fourth slider member 68 such that the fourth slider member 68 moves laterally when it is displaced.

As described above, the cams 40 extending from the movable member 36 can displace the first slider member 50, the second slider member 52, the third slider member 66, and the fourth slider member 68 laterally, or outwardly, away from the longitudinal center of the first jaw 30 and the second jaw 32. In various embodiments, the cams 40 can engage the slider members 50, 52, 66, and 68 simultaneously, or at least substantially simultaneously, and displace the slider members 50, 52, 66, and 68 at the same time. In such embodiments, further to the below, the first slider member 50 and the second slider member 52 can comprise a first pair of slider members which can tension tissue in a first direction and the third slider member 66 and the fourth slider member 68 can comprise a second pair of slider members which can tension tissue in a second direction, which can be opposite the first direction, for example. In at least one such embodiment, the first pair of slider members 50 and 52 and the second pair of slider members 66 and 68 can pull in the tissue in different directions at the same time. In various other embodiments, the slider members 50, 52, 66, and/or 68 can be displaced sequentially. In at least one such embodiment, the first pair of slider members 50 and 52 can be displaced laterally before the second pair of slider members 66 and 68 are displaced laterally, for example. In certain embodiments, the cams 40 can be positioned on the movable member such that the cams 40 that engage the third slider member 66 and the fourth slider member 68 are staggered proximally behind the cams 40 that engage the first slider member 50 and the second slider member 52.

In at least one embodiment, referring to FIGS. 2A-4, 5, 6, and 6A, the surgical instrument can further comprise a first guide 62 which can be positioned in elongate shaft 12 and/or the end-effector 16 which can be configured to support the movable member 36 as the movable member 36 is moved proximally and/or distally within the end-effector 16. In at least one such embodiment, the distal end 20 of the elongate shaft 12 can house the first guide 62. In various embodiments, a second guide 64 can be positioned within the elongate shaft 12 to support the tube 35. In various embodiments, the first guide 62 and/or the second guide 64 can also receive therethrough the conductive element 46 and/or the return conductive element (not illustrated) which can complete the energy circuit with the electrode or the electrodes of the end-effector 16, as discussed in greater detail herein. In at least one embodiment, the tube 35 can act as the return conductor for returning energy from the second electrode 45.

In one embodiment, again referring to FIGS. 2A-4, 5, 6, and 6A, the fuse 33 can be positioned over the electrode 45 of the second jaw 32. Although the fuse 33 is described as being positioned on the second jaw 32, it can also be positioned on the first jaw 30 or on both of the first jaw 30 and the second jaw 32. In other embodiments, the fuse 33 can also be positioned on at least portions of the movable member 36. As discussed above, the fuse 33 can be comprised of a PTC material. As the PTC material increases in temperature, in various circumstances, its electrical impedance can increase. Thus, the PTC material can become power limiting when the temperature of the PTC material rises above a desired level and, thus, the impedance can rise to a level in which the flow of current between the electrodes is substantially reduced. In one embodiment, if the PTC material is used, a constant energy supply can be used. Examples of the various PTC materials and their functions are described in greater detail in U.S. Pat. No. 5,624,452 to Yates, entitled HEMOSTATIC SURGICAL CUTTING OR STAPLING INSTRUMENT, U.S. Pat. No. 6,929,644 to Truckai et al., entitled ELECTROSURGICAL JAW STRUCTURE FOR CONTROLLED ENERGY DELIVERY, U.S. Pat. No. 6,770,072 to Truckai et al., entitled ELECTROSURGICAL JAW STRUCTURE FOR CONTROLLED ENERGY DELIVERY, and U.S. Pat. No. 6,929,622 to Chian, entitled SAFETY SYRINGE CYLINDER, the entire disclosures of which are hereby incorporated by reference. The use of various PTC materials in electrosurgical instruments is also described in U.S. Pat. No. 7,112,201 entitled ELECTROSURGICAL JAW STRUCTURE FOR CONTROLLING ENERGY DELIVERY and U.S. Pat. No. 6,929,622 entitled ELECTROSURGICAL JAW STRUC- TURE FOR CONTROLLED ENERGY DELIVERY, the entire disclosures of which are incorporated herein by reference.

In one embodiment, temperature measuring devices or sensors, such as thermocouples, RTD's (resistive thermal devices), thermistors, and/or other suitable devices can be embedded at strategic locations within the end-effector 16 to sense the temperature of the tissue positioned within the end-effector 16. In certain embodiments, the delivery of energy to at least one of the electrodes can be controlled in response to feedback from these devices, for example.

In one embodiment, the energy source 11 can deliver energy to the conductive element 46, the electrode 44, the electrode 45, and/or a return conductive element. In various embodiments, the actuation button 26 can be operably engaged with a switch to allow the energy to pass from the energy source 11 to the conductive element 46 and thereby to the electrode 44 when the actuation button 26 is actuated or depressed. In certain embodiments, energy can flow to the electrode 44 until the button 26 is released. In at least one embodiment, the actuation button 26 can allow energy to flow to the electrode 44 for a predetermined suitable period of time regardless of how long the actuation button 26 is depressed by the surgeon. Such a feature can ensure that adequate energy is supplied to the tissue to create a suitable seal in the tissue. In one embodiment, the predetermined suitable period of time can be based on the thickness of the tissue clamped within the end-effector 16.

In one embodiment, the path of the energy can be from the energy source 11, to the conductor 15, through the switch, to the conductive element 46, to the electrode 44, through the tissue clamped within the end-effector 16 (i.e., through the first region of the tissue), through the fuse 33, to the return electrode 45 (e.g., portions of the second jaw 32), through a return conductor, through the conductor 17 and back to the energy source 11, thereby completing the circuit of the energy source 11 with the end-effector 16.

In one embodiment, heat can be generated in the end-effector 16 when electrical energy is provided to the end-effector 16 during the tissue-sealing process. More particularly, owing to the impedance, or resistance, of the tissue positioned intermediate the electrodes 44 and 45 of the end effector 16, heat can be generated within the tissue as the current is flowing therethrough. As discussed above, such heat can denature the collagen within the tissue positioned intermediate the electrodes 44 and 45. In various circumstances, however, the heat can spread from the regions of the tissue being sealed between the electrodes 44 and 45 (i.e., the sealing region) into the tissue surrounding or adjacent to the region of the tissue being sealed (i.e., the surrounding region). Such thermal spreading into the surrounding region may not be desirable in certain circumstances in that the heat can over-denature the collagen in, and/or otherwise damage, the surrounding tissue. As a result, in some instances, it may be desirable to tension the surrounding tissue in order to reduce the denaturation thereof. Further to the above, tensioning, or applying tensile stresses or loads to, the tissue in the surrounding region of tissue can decrease, or possibly exponentially decrease, the rate at which the thermal damage to the surrounding tissue can occur. More specifically, tensioning the surrounding tissue can decrease, or possibly exponentially decrease, the amount in which the surrounding tissue shrinks during the sealing process. As such, it may be desirable to tension or apply a mechanical stress or load to the surrounding tissue to reduce the rate at which thermal damage occurs in the surrounding tissue.

Figure 6:
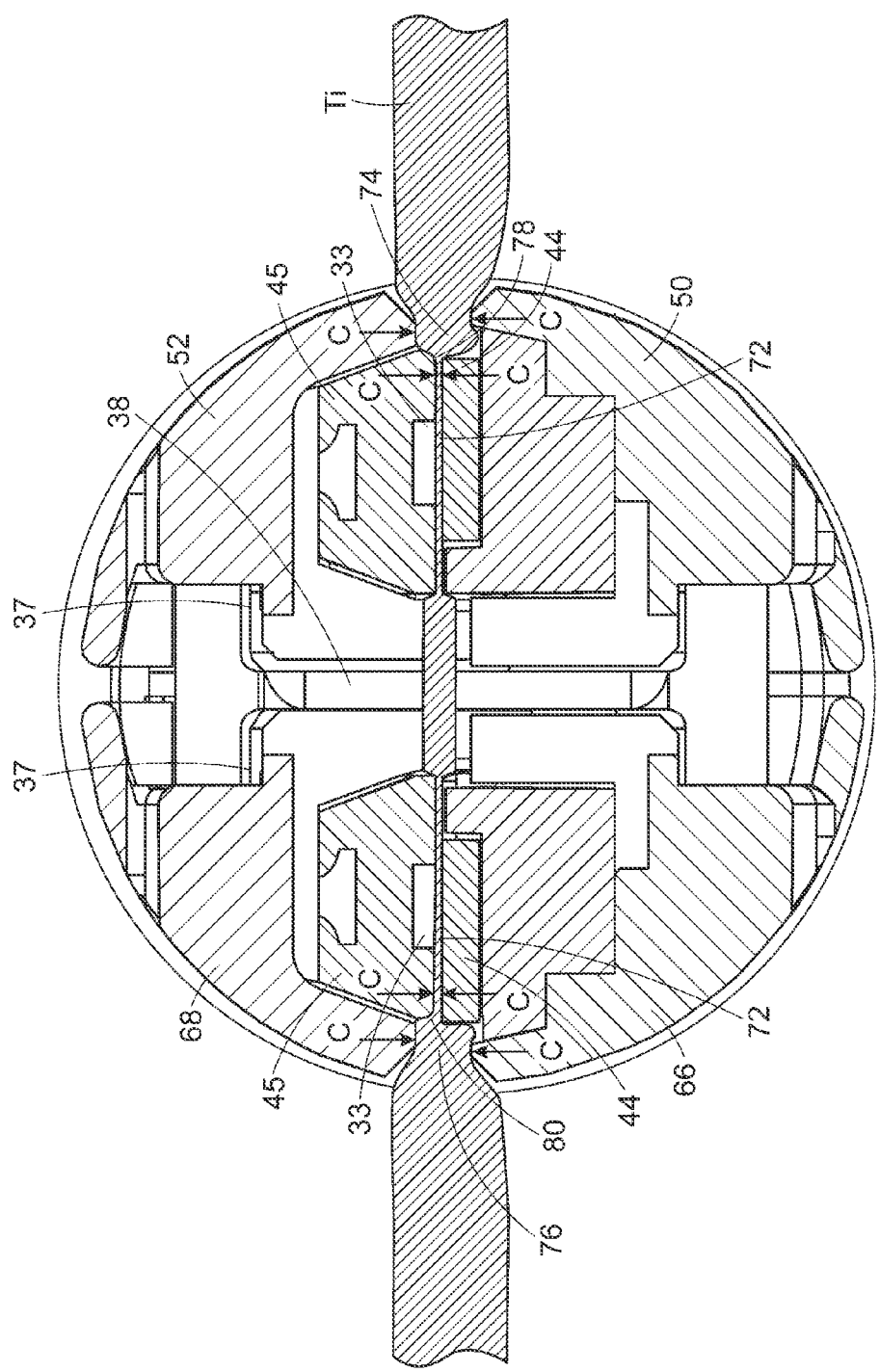
FIG. 6 is a cross-sectional view of the end-effector of FIG. 3A taken along line 6-6 in accordance with at least one non-limiting embodiment of the present disclosure.
Figure 6A:
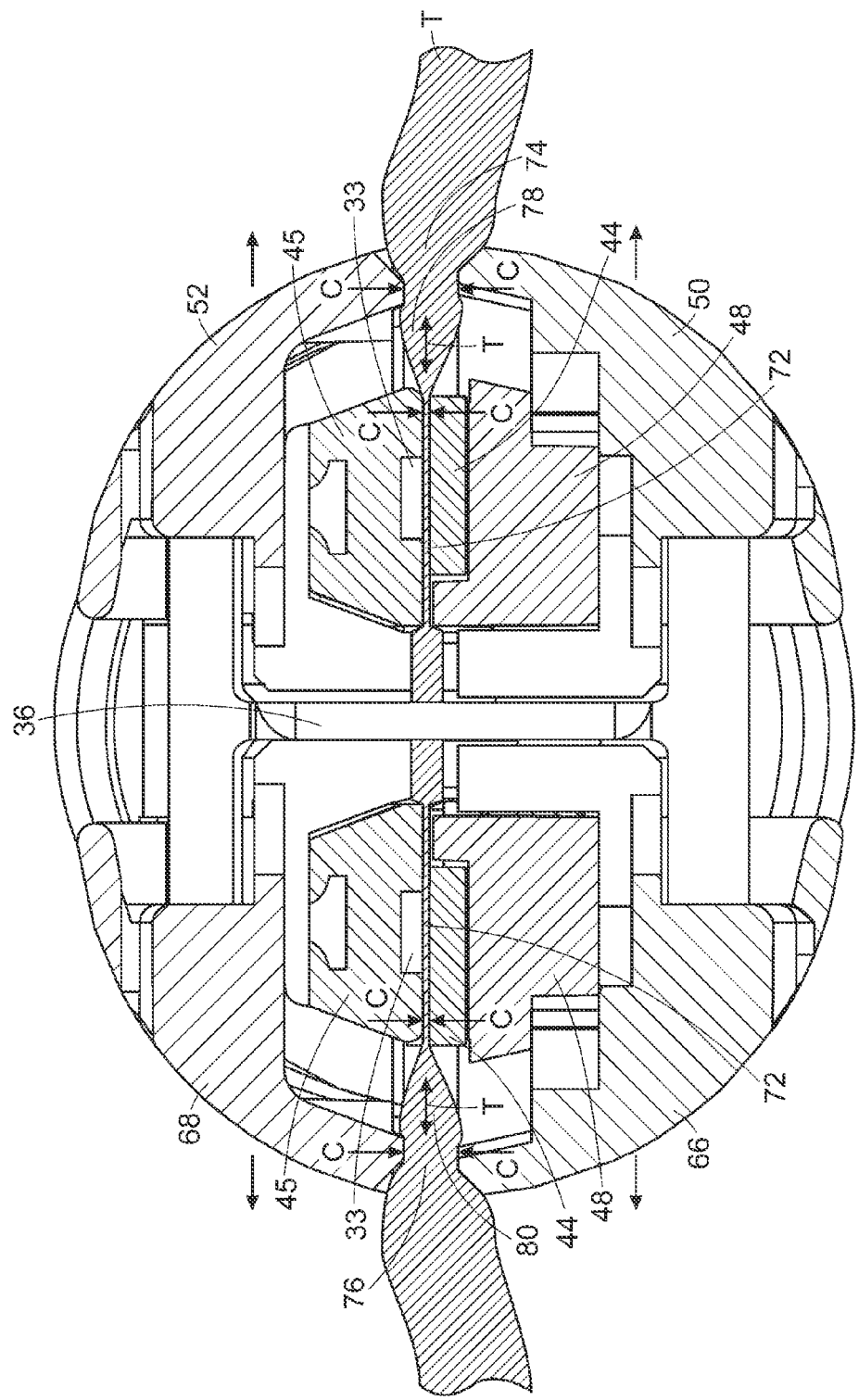
FIG. 6A is a cross-sectional view of the end-effector of FIG. 4 taken along line 6A-6A in accordance with at least one non-limiting embodiment of the present disclosure.

In view of the above, referring to FIGS. 6 and 6A, the surgical instrument 10 of the present disclosure can be configured to tension tissue (indicated as "T") surrounding the first region of tissue 72 being sealed by the end-effector 16 using the first, second, third, and/or the fourth slider members 50, 52, 66, and 68. In one embodiment, less than all of the first, second, third, and/or the fourth slider members 50, 52, 66, and 68 may be used to tension the tissue. In one embodiment, for example, the first and second slider members 50 and 52 can be used to tension the tissue, while in other embodiments, the third and fourth slider members 66 and 68 can be used to tension the tissue. In at least one such embodiment, a surgical instrument can comprise a first movable member which can be displaced distally to actuate the first and second slider members 50 and 52 and a second movable member which can be displaced distally to actuate the third and fourth slider members 66 and 68 wherein the first movable member and the second movable member can be actuated independently.

In one embodiment, referring to FIGS. 4-8, the first slider member 50 and the second slider member 52 can be movable laterally relative to the longitudinal axis defined between the first end of the electrode 44 and the second end of the electrode 44. In various embodiments, as described above, the first slider member 50 and the second slider member 52 can move relative to and/or away from the electrode 44 in a first direction and the third slider member 66 and the fourth slider member 68 can move relative to and/or away from the electrode 44 in a second direction. In one embodiment, as also described above, the first direction can be opposite, or substantially opposite, to the second direction.

In various embodiments, referring to FIGS. 3A-8, the movable member 36 can be configured to engage the first jaw 30 and the second jaw 32 when the movable member 36 is advanced distally within the end-effector 16 to compress the first region of the tissue 72. As described above, the movable member 36 can be configured to bias the first slider member 50 relative to and/or away from the electrodes 44 and 45 and can be configured to bias the second slider member 52 relative to and/or away from the electrode 44 and 45. As also described above, such biasing can be accomplished by the cams 40 or other members on the distal portion of the movable member 36. In one embodiment, the first slider member 50 and the second slider member 52 can be moveable relative to the axis of the electrode 44 between a first, unextended position (see e.g., FIGS. 3A, 6, and 7) and a second, extended position (see e.g., FIGS. 4, 5, 6A, and 8). The first and second slider member 50 and 52 can be further away from the longitudinal axis of the electrode 44 when in the second, extended position than when in the first, unextended position. Similarly, in one embodiment, the third slider member 66 and the fourth slider member 68 can be moveable relative to the axis of the electrode 44 between a first, unextended position (see e.g., FIGS. 3A, 6, and 7) and a second, extended position (see FIGS. 4, 5, 6A, and 8). The third and fourth slider members 66 and 68 can be further away from the longitudinal axis of the electrode 44 when in the second, extended position than when in the first, unextended position.

In one embodiment, further to the above, the movable member 36 can be a cutting member configured to cut the tissue within the first region of the tissue 72. The cutting member can be configured to engage the first jaw 30 and the second jaw 32 when the cutting member is advanced distally within the end-effector 16 to compress and cut or score the first region of the tissue 72. The cutting member can be configured to act against and/or bias the various slider members to move the various slider members relative to, away from, and/or toward the electrode 44. In such an embodiment, the cutting member can comprise cams, similar to cams 40, described above. Other details of the cutting member's engagement with the various slider members can be the same as or similar to the engagement of the movable member 36 with the various slider members described herein.

In one embodiment, referring to FIGS. 6 and 6A, the electrode 44 and the fuse 33 can engage the first region of tissue 72 compressed (indicated as "C") within the end-effector 16 when the second jaw 32 is moved into the closed position. The first and the second slider members 50 and 52 can each comprise a tissue-contacting surface configured to engage the second region of the tissue 74. Likewise, the third and fourth slider members 66 and 68 can each comprise a tissue-contacting surface configured to engage the third region of the tissue 76. Upon closure of the second jaw 32, the first and second slider members 50 and 52 can engage the second region of the tissue 74 and the third and fourth slider members 66 and 68 can engage the third region of tissue 76. A first non-engaged portion of tissue 78 can be present intermediate the first region of the tissue 72 and the second region of the tissue 74 and a second non-engaged portion of tissue 80 can be present intermediate the first region of the tissue 72 and the third region of the tissue 76. In use, the first non-engaged portion of tissue 78 can be tensioned by the first and second slider members 50 and 52 when they are moved relative to and/or away from the electrode 44. Stated another way, the first and second slider members 50 and 52 can apply a tensile force to the first non-engaged portion of tissue 78 when they are moved relative to and/or away from the electrode 44. The second non-engaged portion of tissue 80 can be tensioned by the third and the fourth slider members 66 and 68 when they are moved relative to and/or away from the electrode 44. Stated another way, the third and fourth slider members 66 and 68 can apply a tensile force to the second non-engaged portion of tissue 80 when they are moved relative to and/or away from the electrode 44. In one embodiment, this tensioning can occur by the cams 40, or other structures, of the movable member 36 engaging the various slider members and moving them relative to and/or away from the electrode 44 and the fuse 33, and/or relative to and/or away from the longitudinal axis of the electrode 44 and/or the end-effector 16. The cams 40 can engage the various slider members when the movable member 36 is advanced proximally to distally within the end-effector 16 when the trigger 24 is retracted. In one embodiment, the trigger 24 can be retracted more than one time to fully advance the movable member 36.

When energy is supplied by the energy source 11 to the electrode 44 on the first jaw 30, the energy can pass through the first region of the tissue 72 and then flow through the fuse 33 to the electrode 45 on the second jaw 32. This passage of energy through the first region of tissue 72 can generate heat within the first region of the tissue 72 which heat can extend toward, to, or beyond the second region of tissue 74 and/or the third region of tissue 76. As such, the heat can also extend into the first non-engaged portion of the tissue 78 and the second non-engaged portion of the tissue 80, for example, and then outwardly therefrom. Tensioning of the first and second non-engaged portions of the tissue 78 and 80 can reduce the spread of thermal damage from the first region of tissue 72 as the rate of thermal damage at a given temperature is reduced in the presence of increased tensile stresses within the tissue. In one embodiment, the tensioning of the first and second non-engaged portions of the tissue 78 and 80 can reduce the spread of thermal damage beyond the second and third regions of tissue 74 and 76, for example.

As described above, referring to FIGS. 4-5, some or all of the first, second, third, and fourth slider members 50, 52, 66, and 68 can comprise a camming surface which can be engaged by a cam extending from the movable member 36, for example. In at least one embodiment, the first slider member 50 can comprise a first camming surface 90 and the second slider member 52 can comprise a second camming surface 92 (FIG. 2A) wherein a channel 94 can be defined intermediate the first camming surface 90 and the second camming surface 92. In at least one such embodiment, a cam track 96 can extend along one or both sides of the channel 94. Similarly, the third slider member 66 can comprise a first camming surface 90 and the fourth slider member 68 can comprise a second camming surface 92 wherein a channel 94 can be defined intermediate the first camming surface 90 and the second camming surface 92. In at least one such embodiment, a cam track 96 can extend along one or both sides of the channel 94. In use, as described in greater detail below, the cams 40 of the movable member 36 can be movably received within the channels 94 as the movable member 36 is moved distally.

Further to the above, the various slider members of the end-effector 16 can be in their first, unexpanded position prior to the end-effector 16 being closed. When the trigger 24 is retracted to advance the movable member 36 distally within the end-effector 16, the cams 40 can engage and move along the channels 94 and contact the first camming surfaces 90 and the second camming surfaces 92. Through contact with the camming surfaces and the distal movement of the movable member 36, the various slider members can be moved relative to and/or away from the electrodes 44 and 45, relative to and/or away from the longitudinal axis of the end-effector 16, and/or relative to and/or away from the cutting member slots 60 and 60'. Such movement can cause the various slider members to tension the first and second non-engaged portions of the tissue 78 and 80 and reduce the spread of thermal damage outside of the first and second non-engaged portions of tissue 78 and 80. As the cams 40 progress distally within the end-effector 16, they can engage the cam tracks 96 to maintain the various slider members in the second, expanded position (i.e., the tensioned position). In various circumstances, the biasing members 56 and 56' can limit the displacement of the slider members to assure that the slider members are not over-extended, or moved too far away from the first region of tissue 72, as the over tensioning of the tissue could possibly tear the first and second non-engaged portions of the tissue 78 and 80, for example.

In at least one embodiment, after the movable member 36 has been sufficiently advanced and the first region of tissue 72 has been sufficient sealed and incised, a release button (not illustrated) on the handle portion 22 can be depressed to allow the movable member 36 to move proximally with respect to the end-effector 16. While the movable member 36 is being moved proximally, the cams 40 can move proximally along the cam tracks 96 of the various slider members until the cams 40 are sufficiently disengaged from the first camming surfaces 90 and the second camming surfaces 92. Thereafter, the biasing member 56 of the first jaw 30 can pull the first slider member 50 and the third slider member 66 inwardly toward one another and, similarly, the biasing member 56' of the second jaw 32 can pull the second slider member 52 and the fourth slider member 68 inwardly toward one another. In such circumstances, the various slider members can move relative to and/or toward the electrodes 44 and 45 and/or relative to and/or toward the longitudinal axis of the end-effector 16 and return the slider members to their first, or unexpanded, position (see e.g., FIG. 3A).

In certain alternative embodiments, further to the above, only the first and second slider members 50 and 52 may be movable relative to and/or away from the electrode 44 such that only the first non-engaged portion 78 is tensioned upon the distal movement of the movable member 36 within the end-effector 16. In such an embodiment, the end-effector may not comprise the third and fourth slider members 66 and 68, but instead, the end-effector may comprise third and fourth fixed members. In other embodiments, the cams 40 may not be provided on one side of the movable member 36 such that the third and fourth slider members 66 and 68 are not moved into their second, expanded position upon distal movement of the movable member 36 within the end-effector 16. In other embodiments, only the third and fourth slider members 66 and 68 may be movable relative to, away from, and/or toward the electrode 44 to tension the second non-engaged portion of tissue 80.

Figure 7:
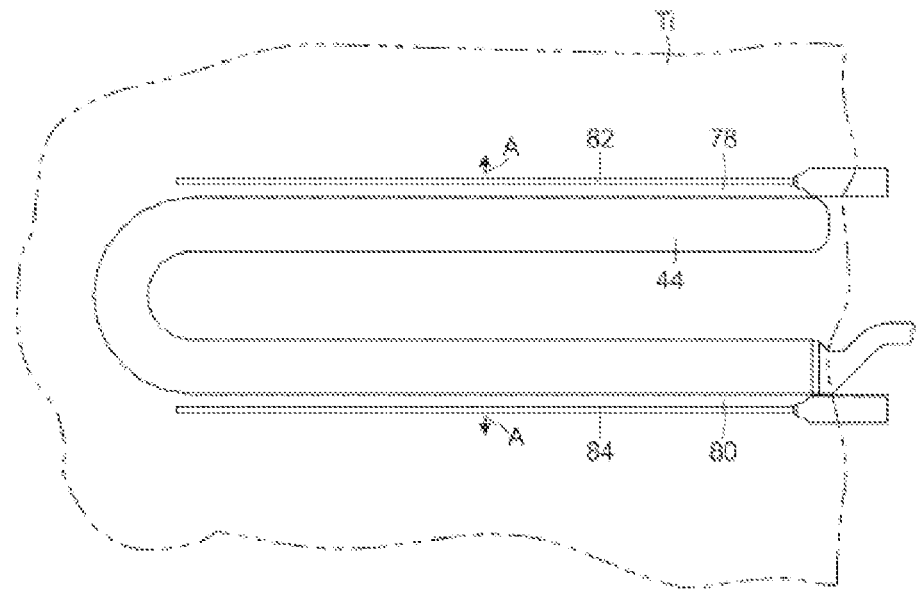
FIG. 7 is a schematic illustration of portions of an end-effector engaging tissue in a first, unextended position in accordance with at least one non-limiting embodiment of the present disclosure.
Figure 8:
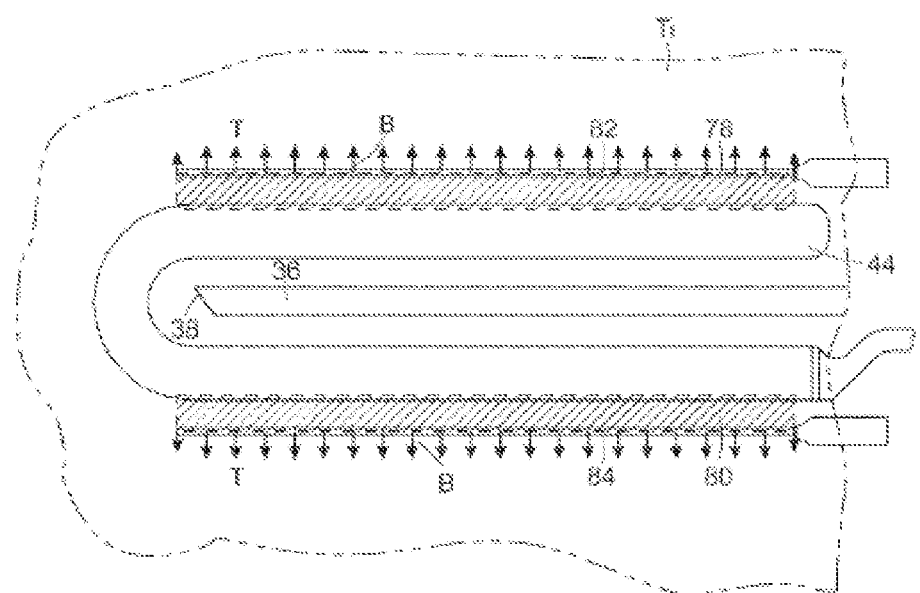
FIG. 8 is a schematic illustration of the portions of the end-effector of FIG. 7 engaging tissue in a second, extended position in accordance with one non-limiting embodiment of the present disclosure.
Figure 9:
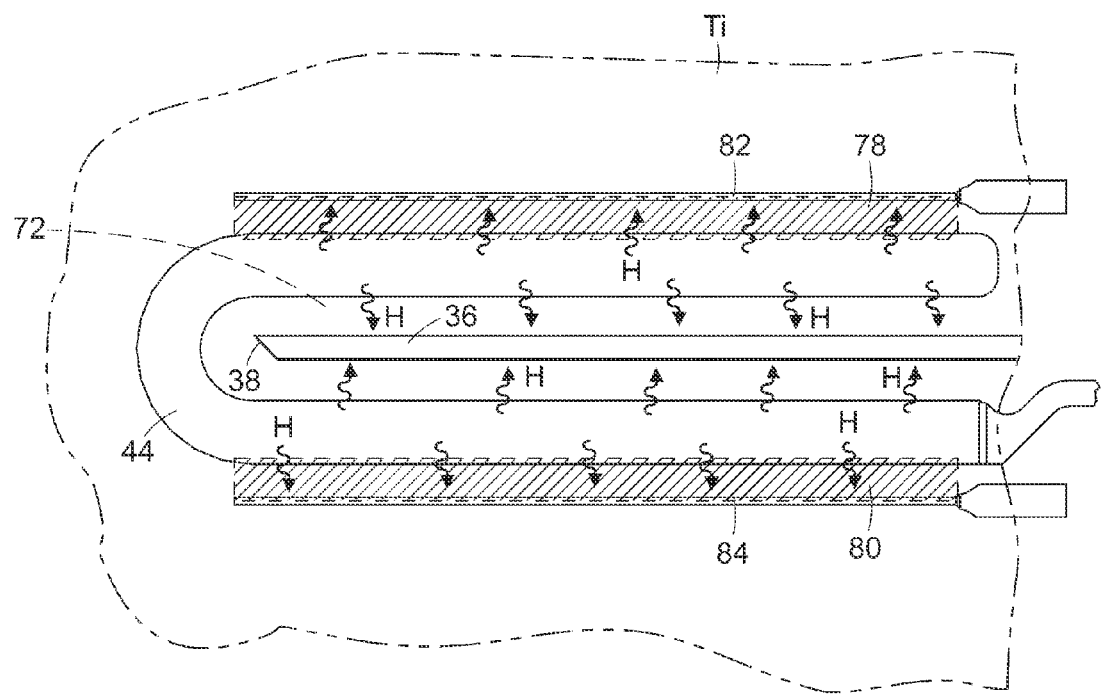
FIG. 9 is a schematic illustration of the portion of the end-effector of FIG. 8 when energy is applied to one or more electrodes within the end-effector in accordance with at least one non-limiting embodiment of the present disclosure.
Figure 10:
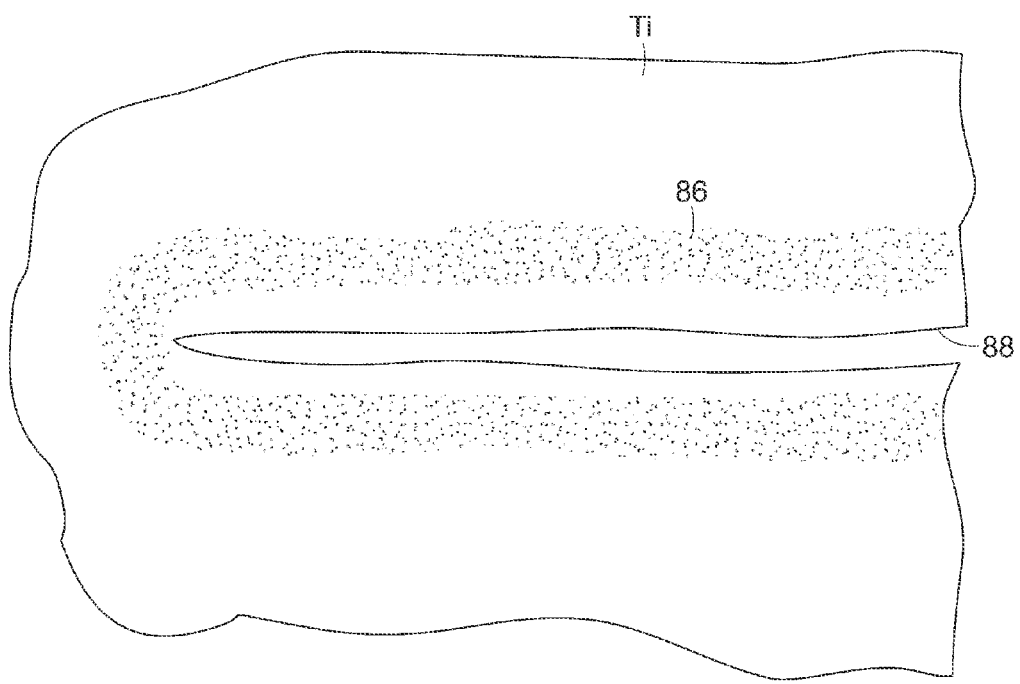
FIG. 10 is a schematic illustration of the tissue illustrated in FIG. 9 after the tissue has been sealed, tensioned, and incised in accordance with at least one non-limiting embodiment of the present disclosure.

In one embodiment, referring to FIGS. 7-10, schematic top view illustrations of the various tissue cutting, sealing, and tensioning steps undertaken by the end-effector 16 are provided. Not all of the components of the end-effector are shown in FIGS. 7-10 for clarity in illustration. FIG. 7 illustrates the end-effector in a closed position wherein the various slider members of the end effector are in the first, unextended position. The tissue compression points 82 and 84 of the various slider members are illustrated proximate to the electrode 44. The tissue compression point 82 can be between a tissue-contacting surface of the first slider member 50 and the second slider member 52 and the tissue compression point 84 can be between a tissue-contacting surface of the third slider member 66 and the fourth slider member 68 (see e.g., FIGS. 6 and 6A). Arrows "A" indicate one possible direction of movement of the tissue compression points 82 and 84 relative to the electrode 44 to tension the first and second non-engaged tissue portions 78 and 80. FIG. 8 illustrates the end-effector in a closed position with the various slider members in their second, extended position and the cutting member 38 and the movable member 36 advanced distally within the end-effector. Arrows "B" indicates one possible direction in which the various slider members tension the first and second non-engaged portions of the tissue 78 and 80. FIG. 9 illustrates energy, such as Rf energy, for example, being applied to the first region of the tissue 72 contacting the electrode 44 and heat ("H") spreading from the first region of the tissue 72. In FIG. 9 the cutting member 38 and the movable member 36 continue to be advanced distally within the end-effector. FIG. 10 illustrates the tissue after it has been tensioned, sealed, and cut, for example. The seal is indicated as 86 and the cut line is indicated as 88.

In one embodiment, although not illustrated, the end-effector 16 can be configured to deploy staples and/or other permanent fasteners, for example, into the first region of the tissue 72 and/or any other suitable region of tissue. It is also conceived that these fasteners may be made of an absorbable or dissolvable material such as Vicryl and/or iron, for example. Other materials could include PDS, PLA, and/or any other suitable polymer and/or magnesium and/or any other suitable metal, for example. In various embodiments, the movable member 36 can comprise a staple driver on a distal end or portion thereof, for example. The first jaw 30 can be configured to receive a staple cartridge comprising one or more staples or rows of staples and the second jaw 32 can comprise one or more anvil pockets or rows of anvil pockets configured to receive the legs of one or more staples therein to deform the staples as they are deployed. The anvil pockets can be aligned with staple cavities in the staple cartridge such that the staple legs can be deformed when the staples are deployed from the staple cartridge. In one embodiment, the staples can be fired or deployed from the staple cartridge using the staple driver. In various embodiments, the staple driver can be energized by the energy source 11, or another energy source such that, when the staple driver contacts the one or more staples, the staples can be energized to form a seal in the tissue where the staple legs puncture the tissue. In such an embodiment, the staples and the staple driver can comprise electrically conductive materials. In various embodiments, the electrode 45 on the second jaw 32 can act as the return electrode such that energy can flow from the staples, through the fuse 33, to the electrode 45 and then be returned to the energy source 11.

In various embodiments, the cutting member 38 and/or portions of the movable member 36 can be energized by the energy source 11, for example, such that as the cutting member 36 cuts the first region of tissue 72, as described above, a seal can be created at the edges of the cut line. Here, the energy from the cutting member 38 can pass through the tissue, to the fuse 33, to the electrode 45, and back to the energy source 11. In various embodiments, as described above, the flow of current through the tissue can be controlled by the actuator button 26 which can be actuated before, during, and/or after the tissue is tensioned as described herein.

Figure 11:
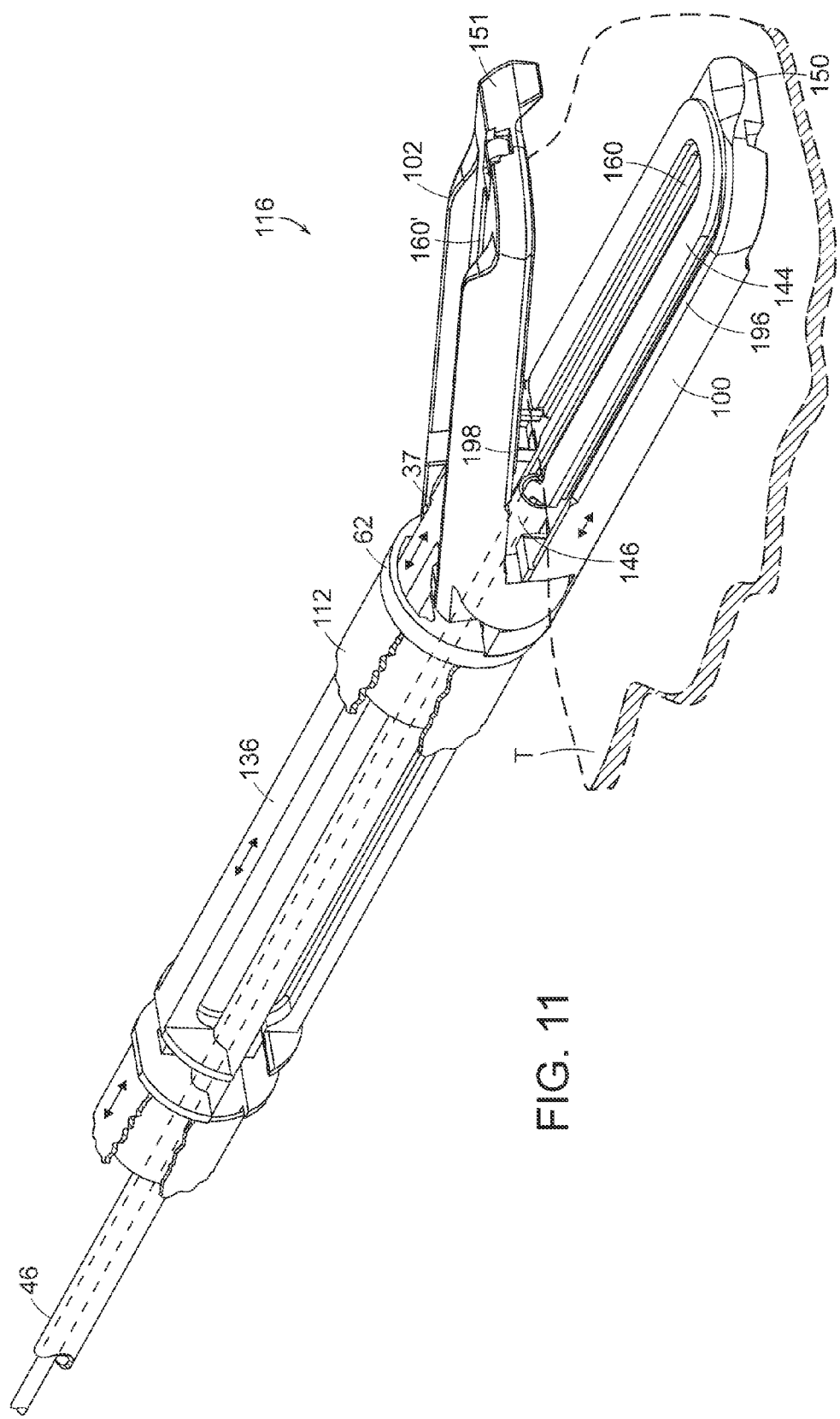
FIG. 11 is a perspective view of an end-effector and a portion of a surgical instrument in accordance with at least one non-limiting embodiment of the present disclosure.
Figure 12:
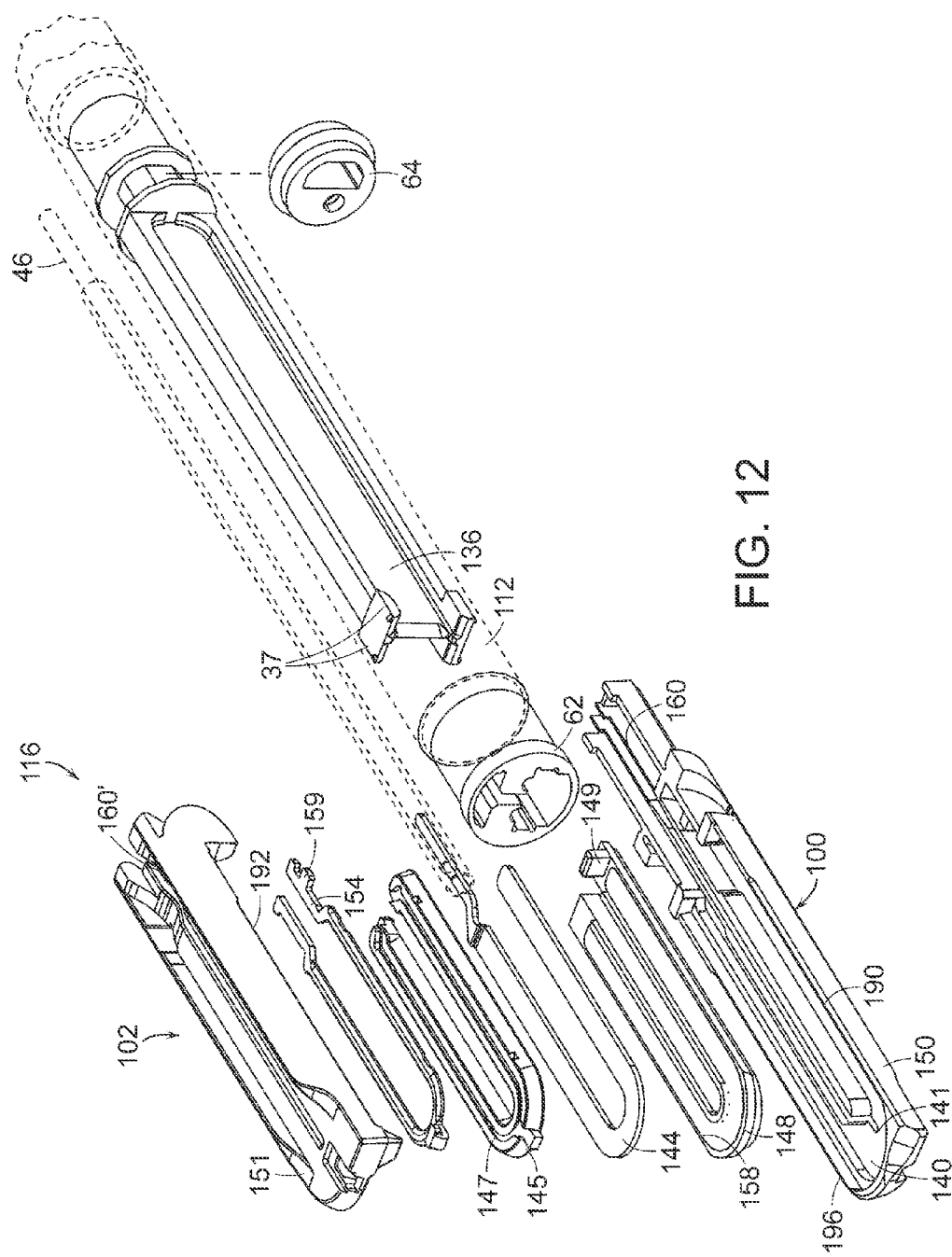
FIG. 12 is an exploded perspective view of the end-effector of FIG. 11 in accordance with at least one non-limiting embodiment of the present disclosure.

As discussed above, a surgical instrument can comprise an end effector which can be configured to clamp and compress tissue captured within the end effector and then spread or stretch the tissue laterally in order to create tension within the tissue outside the desired region to be sealed. As also discussed above, creating tension within the tissue can reduce the rate at which thermal damage occurs, for example, through the tensioned tissue and, as a result, the spread of thermal tissue damage can be controlled. In various embodiments, a surgical instrument can comprise an end effector configured to stretch the tissue captured therein in any suitable direction. Referring now to FIGS. 11 and 12, a surgical instrument can comprise an end effector 116 which can comprise, similar to the above, a first jaw 100 and a second jaw 102 wherein the second jaw 102 can be rotated, or pivoted, relative to the first jaw 100 between open and closed positions, for example. In at least one such embodiment, the surgical instrument can further comprise a movable member 136 which can be displaced distally to contact the second jaw 102 and pivot the second jaw 102 downwardly. Thereafter, the movable member 136 can be advanced through the longitudinal slots 160 and 160' defined in the first jaw 100 and the second jaw 102, respectively, and incise the tissue captured between the first jaw 100 and the second jaw 102. In various embodiments, as described in greater detail below, the distal advancement of the movable member 136 can cause portions of the end effector 116 to be displaced distally and, as a result, stretch or tension the tissue longitudinally.

Referring now to FIGS. 13A-13D, a surgical instrument can further comprise a handle 114 and, in addition, a shaft 112 extending from the handle 114. Similar to the above, the handle 114 can comprise a handle portion 122 and a firing trigger 124 operably coupled with the movable member 136. In at least one such embodiment, the firing trigger 124 can be pivotably coupled to the handle portion 122 such that the rotation of the trigger 124 toward the handle portion 122 can move a top portion of the firing trigger 124 distally. In various embodiments, the top portion of the firing trigger 124 can be operably coupled with a firing member 130 such that the distal movement of the top portion of the firing trigger 124 is transmitted to the firing member 130. In such embodiments, the movable member 136 can be coupled to the firing member 130 wherein, as a result, the firing member 130 and the movable member 136 can be moved distally when the trigger 124 is retracted toward the handle portion 122. Referring primarily to FIG. 13A, the firing member 130 and the movable member 136 can be slidably positioned within a frame 110 of the shaft 112. In at least one such embodiment, the frame 110 can comprise an inner side wall 111 which can define an inner longitudinal cavity. In various embodiments, at least a portion of the firing member 130 and/or the movable member 136 can be closely received within the inner longitudinal cavity such that the firing member 130 and the movable member 136 are confined to movement along a longitudinal path defined by the inner side wall 111.

Further to the above, the surgical instrument can be operated through a series of stages between an open, unfired configuration (FIG. 13A) and a closed, fired configuration (FIG. 13D). With regard to FIG. 13A, the firing trigger 124 is illustrated in an unactuated position and the movable member 136 is illustrated in a fully retracted, proximal position indicated by the proximal datum P. As the firing trigger 124 is moved toward the handle 122, referring to FIG. 13B, the trigger 124 can advance the movable member 136 distally past the datum P and into the longitudinal slots 160 and 160' of the jaws 100 and 102, respectively, in order to close the second jaw 102, as described above. The reader will note that the movable member 136 has only been partially advanced in FIG. 13B and may be returned to its retracted position illustrated in FIG. 13A in order to reopen the second jaw 102. In such circumstances, the movable member 136, and/or any cutting edge on the movable member 136, may not contact the tissue captured between the first jaw 100 and the second jaw 102 when the movable member 136 has only been advanced to its position illustrated in FIG. 13B. The reader will also note, when comparing FIGS. 13A and 13B, that the firing member 130 is configured to move relative to the shaft frame 110 when the firing member 130 is moved between its positions illustrated in FIGS. 13A and 13B, as described in greater detail below.

Referring again to FIG. 13A, the firing member 130 can comprise a detent member 132 which can be positioned within a longitudinal detent slot 113 defined in the shaft frame 110. In at least one such embodiment, the firing member 130 can further comprise a detent spring 131 which can be configured to bias the detent member 132 into the longitudinal detent slot 113. In various embodiments, the slot 113 can comprise a proximal end 115 and a distal end 117 wherein the detent member 132 can be configured to slide between the proximal end 115 and the distal end 117 of the slot 113 when the firing member 130 is advanced between its position illustrated in FIG. 13A and its position illustrated in FIG. 13B. More particularly, referring to FIG. 13A, the detent member 132 can be positioned adjacent to the proximal end 115 of the slot 113 when the surgical instrument is in an unfired position and, referring now to FIG. 13B, the detent member 132 can be positioned adjacent to the distal end 117 of the slot 113 when the firing member 130 is advanced distally to close the second jaw 102 as described above. In such circumstances, the detent member 132 can slide within the longitudinal detent slot 113 of the shaft frame 110 which can allow the firing member 130 to move relative to the shaft frame 110.

In various embodiments, further to the above, portions of the first jaw 100 and the second jaw 102 can extend from the shaft frame 110 and, thus, when the shaft frame 110 is moved distally, such portions of the first jaw 100 and the second jaw 102 can be moved distally as well. Correspondingly, when the shaft frame 110 is not advanced distally, such portions of the first jaw 100 and the second jaw 102 can be held in position. Comparing FIGS. 13A and 13B once again, the reader will note that the distal end of the first jaw 100, for example, is aligned with distal datum D in both FIG. 13A and FIG. 13B indicating that neither the first jaw 100 nor portions of the first jaw 100 were advanced distally when the firing member 130 and the movable member 136 were advanced distally to close the second jaw 102. Similarly, referring now to FIG. 15A, the distal end of the second jaw 102 can remain aligned with the distal datum D when the firing member 130 and the movable member 136 are advanced distally to close the second jaw 102. Referring now to FIG. 15B, once the firing member 130 has been advanced to close the second jaw 102 and the detent member 132 contacts the distal end 117 of the slot 113, the subsequent distal movement of the firing member 130 can advance the shaft frame 110, and portions of the first jaw 100 and/or the second jaw 102 distally, as described in greater detail below.

Referring to FIG. 13B, further to the above, the detent element 132 can be moved against the distal end 117 of the slot 113 as the second jaw 102 is moved into its closed position by the firing member 130 and the movable member 136. Further movement of the firing trigger 124 toward the handle portion 122 can further advance the firing member 130 and the movable member 136 distally. More particularly, a longitudinal force applied to the firing member 130 by the firing trigger 124 can be transmitted to the shaft frame 110 via the detent member 132 such that, as the firing member 130 is advanced distally, the shaft frame 110 can be advanced distally as well. In such circumstances, the detent member 132 can be at least partially positioned within a guide slot 133 defined in the firing member 130 and, in addition, at least partially positioned against the distal end 117 of the longitudinal slot 113 such that the longitudinal force applied to the firing member 130 can be transmitted to the detent member 132 through a sidewall of the guide slot 133 and to the shaft frame 110 through the interaction of the detent member 132 and the distal end 117 of the longitudinal slot 113. In various embodiments, the surgical instrument can further comprise a detent lock which can be configured to hold the shaft frame 110 in position until a sufficient longitudinal force has been applied to the shaft frame 110 by the detent member 132, as described in greater detail below.

Further to the above, referring to FIGS. 13A and 13B, the shaft frame 110 can further comprise a detent member 128 movably positioned within a guide slot 119 defined in the shaft frame 110 wherein the detent member 128 can be biased into a lock notch 123 defined in the frame 126 of the handle assembly 114 by a spring 121. In various embodiments, the lock notch 123 can be defined by a proximal wall 125 and a distal wall 127 which can be configured to contain the detent member 128 therebetween and hold the shaft frame 110 in position until a sufficient force is applied to the shaft frame 110 to push, or recess, the detent member 128 into the guide slot 119 defined in the shaft frame 110 and allow the shaft frame 110 to slide distally relative to the handle frame 126 as described above. In at least one such embodiment, at least a portion of the detent member 128 can be positioned within the guide slot 119 and, in addition, at least a portion of the detent member 128 can be positioned within the lock notch 123 such that the longitudinal force applied to the shaft frame 110 can be transmitted through a sidewall of the guide slot 119, to the detent member 128, and to the distal wall 127 of the lock notch 123 which can create a reactionary force between the distal wall 127 and the detent member 128 which pushes the detent member 128 into the guide slot. In various embodiments, the detent member 128 can comprise an inclined, conical, and/or curved surface, for example, which can be configured to displace the detent member 128 into the guide slot. In any event, the biasing spring 121 can comprise a spring stiffness sufficient to hold the detent member 128 in the lock notch 123 until a predetermined longitudinal force is applied to the shaft frame 110 wherein, once this predetermined longitudinal force has been exceeded, the entirety of the detent member 128 can be pushed out of the lock notch 123 into the guide slot 119 and the shaft frame 110 can be displaced distally.

Once the detent lock holding the shaft frame 110 to the handle frame 126 has been depressed, or deactivated, in various circumstances, the firing member 130, the movable member 136, and the shaft frame 110 can be advanced distally together, as illustrated in FIG. 13C. As discussed above, portions of the first jaw 100 and/or the second jaw 102 can be mounted to the shaft frame 110 wherein, as a result, such portions of the first jaw 100 and/or the second jaw 102 can be moved distally with the shaft frame 110. In at least one embodiment, referring again to FIGS. 11 and 12, the first jaw 130 can comprise a first jaw frame 150 which can be mounted to the shaft frame 110. In various embodiments, the first jaw frame 150 can comprise a trough 140 which can be configured to receive at least a portion of an electrode 144 and/or an electrode support 148 therein. In at least one such embodiment, the electrode 144, the electrode support 148, and/or the trough 140 can be substantially U-shaped wherein, in at least one embodiment, the trough 140 can comprise an enlarged distal portion 141 which can be configured to permit relative longitudinal movement between the electrode 144 and the first jaw frame 150. Referring again to FIGS. 13B and 13C, the first jaw frame 150, as it is mounted to the shaft frame 110, can be moved distally when the shaft frame 110 is moved distally. In at least one such embodiment, the distal end of the first jaw frame 150 can be moved from a position (FIG. 13B) indicated by distal datum D to a position (FIG. 13C) in which the distal end of the first jaw frame 150 is positioned distally with respect to distal datum D. Upon comparing FIGS. 13B and 13C, the reader will note that neither the electrode 144 nor the electrode support 148 has been advanced distally with the first jaw frame 150. In such an embodiment, the electrode 144 and/or the electrode support 148 can be mounted to a non-movable inner frame extending through the shaft 112, for example. In at least one embodiment, referring to FIG. 12, the electrode support 148 can comprise a retention member 149 extending therefrom which can be engaged with the non-movable inner frame to prevent the electrode support 148, and the first electrode 144 supported within a channel 158 defined in the electrode support 148, from moving longitudinally.

Similar to the above, the second jaw 102 can comprise a portion thereof which is mounted to the shaft frame 110 and advanced distally when the shaft frame 110 is advanced distally. In various embodiments, referring again to FIGS. 11 and 12, the second jaw 102 can comprise a second jaw frame 151, a second electrode 145, and a second electrode support 147. In at least one such embodiment, also similar to the above, the second jaw frame 151 can be mounted to the shaft frame 110 while the second electrode 145 and the second electrode support 147 can be mounted to the non-movable inner frame extending through the shaft 112. In use, referring to FIG. 15A, the distal end of the second jaw frame 151 can be aligned with the distal datum D before the shaft frame 110 is advanced distally wherein, referring to FIG. 15B, the distal end of the second jaw frame 151 can be positioned distally with respect the distal datum D after the shaft frame 110 has been advanced. In certain embodiments, referring again to FIG. 12, the electrode support 148 can be retained to the second jaw frame 151 by a retention clip 154 which can, one, hold the electrode support 148 to the second jaw frame 151 when the second jaw 102 is rotated between open and closed positions and, two, allow the second jaw frame 151 to slide distally relative thereto. In at least one such embodiment, the retention clip 154 can comprise a retention member 159 extending therefrom which can be engaged with the inner shaft frame to permit the rotation of, but prevent the longitudinal displacement of, the clip 154.

As discussed above, the longitudinal displacement of various portions of the first jaw 100 and the second jaw 102 can create tension within the tissue. To create such tension, in various circumstances, a portion of the jaws 100 and 102 can compress and hold a portion of the tissue in a stationary, or at least substantially stationary, position while, at the same time, a different portion of the jaws 100 and 102 can compress and pull another portion of the tissue distally, for example. In various embodiments, referring to FIGS. 11 and 12 once again, a portion of the tissue can be compressed between the first electrode 144 and the second electrode 145 and, as the electrodes 144 and 145 are not displaced distally in this embodiment, the tissue compressed between the electrodes 144 and 145 can be held in a stationary, or at least substantially stationary, position. In at least one such embodiment, the first and second jaws 100 and 102 can comprise outer compression surfaces which are configured to compress the tissue along the outer edges of the jaws 100 and 102, for example. In certain embodiments, the first jaw frame 150 of the first jaw 100 can comprise a first lateral compression surface 190 and the second jaw frame of the second jaw 102 can comprise a second lateral compression surface 192 which, when the second jaw 102 is moved into a closed position, can be positioned opposite the first lateral compression surface 190 in order to compress tissue therebetween. In various embodiments, the first jaw frame 150 can further comprise a third lateral compression surface 196 and the second jaw frame 151 can further comprise a fourth lateral compression surface 198 which, when the second jaw 102 is moved into a closed position, can be positioned opposite the third lateral compression surface 196 in order to compress tissue therebetween. As the first jaw frame 150 and the second jaw frame 151 are displaced distally with the shaft frame 110, as described above, the portion of the tissue captured between the lateral compression surfaces 190 and 192 and the portion of the tissue captured between the lateral compression surfaces 196 and 198 can be pulled distally relative to the tissue held in place by the electrodes 144 and 145. In such circumstances, some of the tissue captured within the end effector 116 can be stretched or tensioned which can provide the benefits described herein.

As described above, the longitudinal stretching of the tissue can occur as the drive member 130, the movable member 136, and the shaft frame 110 are displaced distally together. As the reader will note when comparing FIGS. 13B and 13C, the first jaw frame 150 and the movable member 136 have moved in concert with one another, i.e., they have been moved the same, or at least substantially the same, distance distally. In various circumstances, the first jaw frame 150, the second jaw frame 151, and the movable member 136 can be advanced distally until a portion of the shaft frame 110 contacts the frame 126 of the handle assembly 114, as illustrated in FIG. 13C. In various embodiments, the shaft frame 110 can comprise a distal stop 129 which can be configured to abut the handle frame 126. At such point, the first jaw frame 150 and the second jaw frame 151 may have reached the end of their displacement stroke and may not be displaced further distally and, correspondingly, the tissue captured between the first jaw 100 and the second jaw 102 may not be furthered tensioned. Although the first and second jaw frames 150 and 151 may have reached the end of their stroke when the shaft frame 110 contacts the handle frame 126, the reader will note that the movable member 136 may have not yet completed its full firing motion to transect the tissue captured between the first jaw 100 and the second jaw 102. In such circumstances, the firing member 130 and the movable member 136 can be configured to uncouple from the shaft frame 110 such that the firing member 130 and the movable member 136 can move relative to the shaft frame 110 and complete the firing motion of the movable member 136, as illustrated in FIG. 13D.

In order to permit the firing member 130 and the movable member 136 to be advanced distally relative to the shaft frame 110, as described above, the detent member 132 can abut the distal end 117 of the slot 113 and, in response to the longitudinal force applied the firing member 130 by the firing trigger 124, the detent member 132 can be depressed inwardly into the guide slot 133 defined in the firing member 130. In such circumstances, the detent member 132 can slide out of the longitudinal detent slot 113 and slide relative to the shaft frame 110. In at least one such embodiment, the detent member 132 can comprise an inclined, conical, and/or curved surface, for example, which can be configured to bias the detent member 132 into the guide slot 133 when the detent member 132 abuts the distal end 117 of the longitudinal slot 133. As the detent member 132 is biased inwardly, the detent member 132 can compress the spring 131 positioned intermediate the detent member 132 and a base of the guide slot 133. Once the detent has been deactivated, the firing trigger 124 can be moved toward the handle portion 122 until the firing trigger 124 has reached its fully-retracted, fully-fired position. The reader will note from the above that the longitudinal force applied to the firing member by the trigger 124 can deactivate detent 128 and 132. Thus, springs 121 and 131, respectively, must be carefully selected such that detent 128 is deactivated before detent 132. In at least one such embodiment, the spring 131 can comprise a higher spring stiffness than the spring 121, for example. This order of release may also be accomplished by adjusting the amount of interference within each detent.

The full retraction of the firing member can advance the movable member 136 distally until the distal end of the movable member 136 has reached the distal end of the slots 160 and 160' defined in the jaws 100 and 102, as illustrated in FIG. 13D. In various other circumstances, the surgeon may not desire to make a full incision and may, as a result, only partially close the firing trigger 124. Whether or not the surgeon decides to fully or only partially advance the movable member 136, the surgeon can release the trigger 124 to allow the trigger 124 to return to an unactuated position. In at least one such embodiment, the surgical instrument can comprise a trigger spring, for example, which can be configured to bias the trigger 124, the firing member 130, and the movable member 136 into an unfired position (FIG. 13A). In certain embodiments, the surgical instrument can comprise a deactivatable retraction lock which can be configured to prevent the retraction of the firing member 130 and the firing member 136 until the retraction lock is deactivated.

When the firing trigger 124 is released, further to the above, the firing trigger 124 can be rotated forward, or away from the handle portion 122. In such circumstances, the top portion of the firing trigger 124 can be rotated proximally and, owing to the operative engagement between the top portion of the firing trigger 124 and the firing member 130, the firing member 130 can be retracted proximally as well. The retraction motion applied to the firing member 130 can be transmitted to the movable member 136 such that the firing member 130 and the movable member 136 can be retracted together. As movable member 136 is retracted, the fins 37 of the movable member can be disengaged from the first jaw 100 and the second jaw 102 which can allow the second jaw 102 to be re-opened to release the tissue. In at least one such embodiment, a jaw spring can be configured to bias the second jaw 102 into an open configuration. At some point during the retraction of firing member 130, the detent member 132 can be realigned with the longitudinal detent slot 113 defined in the shaft frame 110. In such circumstances, the detent spring 131 can bias the detent member 132 into the detent slot 113 wherein further retraction of the firing member 130 can position the detent member 132 against the proximal wall 115 of the detent slot 113. Similar to the above, the detent member 132 can transmit a longitudinal force between the firing member 130 and the shaft frame 110 such that the firing member 130 can drive the shaft frame 110 proximally as the firing member 130 is retracted. When the shaft frame 110 is moved proximally, the first jaw frame 150 and the second jaw frame 151 can be retracted proximally to their unextended positions and, at some point during the retraction of shaft frame 110, the detent member 128 can be realigned with the lock notch 123 defined in the handle frame 126. In such circumstances, the detent spring 121 can bias the detent member 128 into the lock notch 123 and complete the resetting process of the surgical instrument.

Referring again to FIGS. 15A and 15B, as discussed above, the first jaw frame 150 of the first jaw 100 and the second jaw frame 151 of the second jaw 102 can be moved distally relative to the electrodes 144 and 145 in order to stretch or tension the tissue captured between the first jaw 100 and the second jaw 102. In certain alternative embodiments, a portion of the first jaw and/or the second jaw can be moved proximally in order to stretch or tension the tissue. In various embodiments, referring now to FIGS. 16A and 16B, a surgical instrument can comprise an end effector 216 can comprise a first jaw 200 and a second jaw 202 wherein, similar to the above, the second jaw 202 can be rotated relative to the first jaw 200 between open and closed positions. Also similar to the above, the first jaw 200 can comprise a first jaw frame 250 and a first electrode 244 and the second jaw 201 can comprise a second jaw frame 251 and a second electrode 245. Unlike the embodiment described above, however, the first jaw frame 250 and the second jaw frame 251 may not be extendable distally. In at least one such embodiment, the first electrode 244 and the second electrode 245 can be moved from a first, or proximal, position (FIG. 16A) to a second, or distal, position (FIG. 16B). Upon comparing FIG. 16A and FIG. 16B, the reader will note that the distal ends of the electrodes 244, 245 are aligned with distal datum D in their unextended position (FIG. 16A) and extend distally with respect to the distal datum D in their extended position (FIG. 16B). The reader will also note when comparing FIGS. 16A and 16B that the jaw frames 250 and 251 are not extended distally and remain aligned with datum DD when the electrodes 244 and 245 are advanced.

Figure 14A:
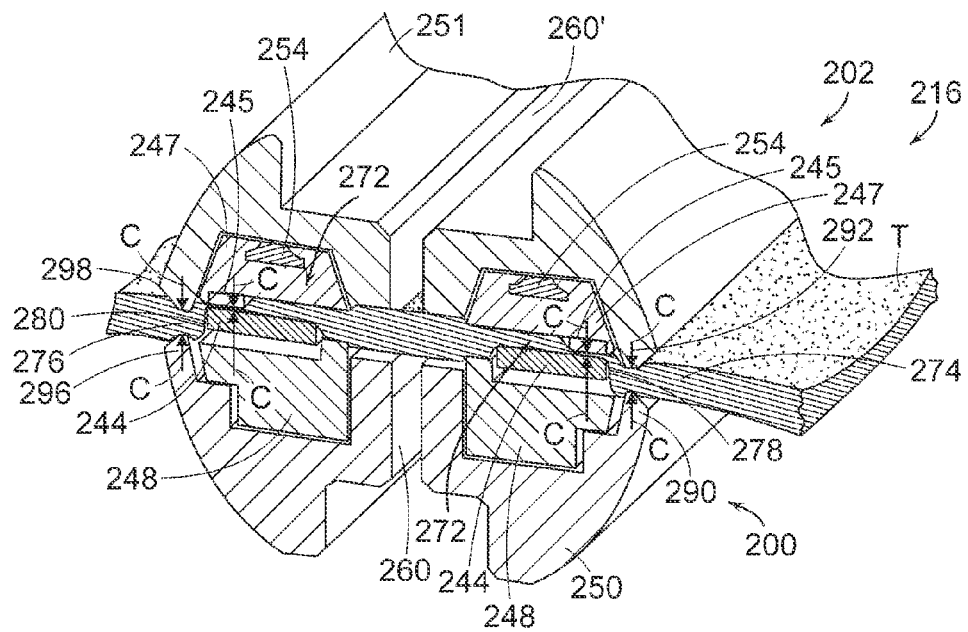
FIG. 14A is a cross-sectional view of an end-effector in accordance with at least one non-limiting embodiment of the present disclosure.
Figure 14B:
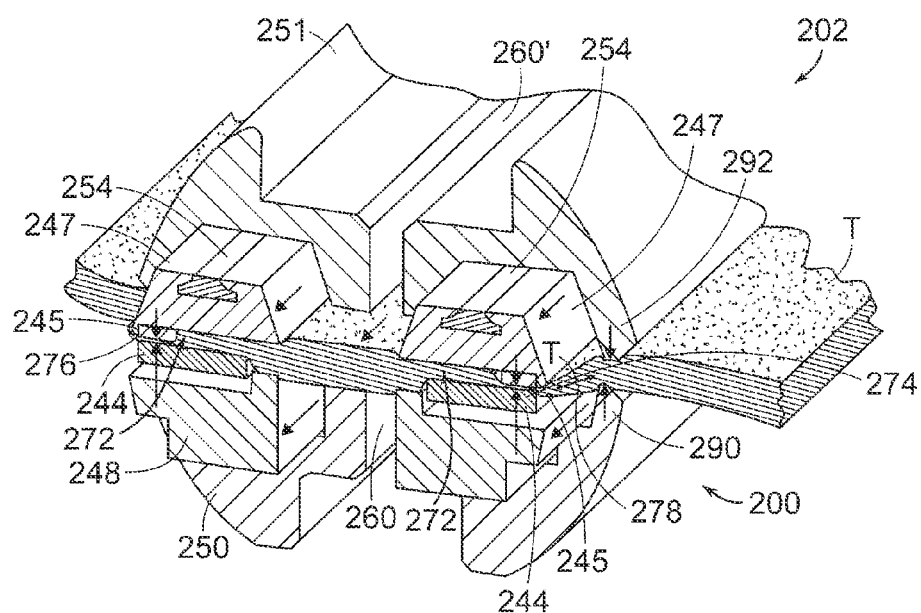
FIG. 14B is a cross-sectional view of the end-effector of FIG. 14A in a closed and extended position in accordance with at least one non-limiting embodiment of the present disclosure.

Referring now to FIGS. 14A and 14B, further to the above, the first jaw 200 can further comprise a first electrode support 248 positioned within the first jaw frame 250 which can be configured to support the first electrode 244. Similarly, the second jaw 202 can further comprise a second electrode support 247 positioned within the second jaw frame 251 configured to support the second electrode 245. In at least one such embodiment, the second jaw 201 can further comprise a clip 254 configured to hold the second electrode support 247 to the second jaw frame 251. In use, the second jaw 201 can be moved into a closed position in which the second electrode 245 contacts the tissue positioned intermediate the first jaw 200 and the second jaw 202 and compresses the tissue against the first electrode 244. The region of tissue compressed between the first electrode 244 and the second electrode 245 is indicated as tissue region 272. Similar to the above, the second jaw frame 251 can comprise a tissue clamping portion 292 which can be positioned opposite a tissue clamping portion 290 of the first jaw frame 250 when the second jaw 201 is rotated into a closed position. In at least one such embodiment, a region of tissue 274 defined along the outer perimeter of the first jaw 200 and the second jaw 202 can be compressed between the tissue clamping portions 290 and 292. Also similar to the above, the second jaw frame 251 can comprise a tissue clamping portion 298 which can be positioned opposite a tissue clamping portion 296 of the first jaw frame 250 when the second jaw 202 is rotated into a closed position. In at least one such embodiment, a region of tissue 276 defined along the outer perimeter of the first jaw 200 and the second jaw 202 can be compressed between the tissue clamping portions 290 and 292.

Once the tissue region has been compressed between the electrodes 244 and 245 and the tissue regions 274 and 276 have been compressed between the clamping portions 290 and 292 and the clamping portions 296 and 298, respectively, the electrodes 244 and 245 can be moved distally with respect to the first jaw frame 250 and the second jaw frame 251, as illustrated in FIG. 14B. In such circumstances, the tissue region 272 can be pulled distally with respect to the tissue regions 274 and 276 in order to pull or tension the regions of tissue positioned therebetween, i.e., tissue regions 278 and 280, respectively. In various embodiments, the first electrode 244 can be moved distally by the first electrode support 248 wherein the first electrode support 248 can be configured to slide within a trough or channel defined in the first jaw frame 250. Similarly, the second electrode 245 can be moved distally by the second electrode support 247 wherein the second electrode support 247 can be configured to slide within a trough or channel defined in the second jaw frame 251. In various embodiments, the first electrode support 248 and the second electrode support 247 can be operably coupled to the shaft frame 110 of the surgical instrument described above. Similarly, the first jaw frame 250 and the second jaw frame 251 can be mounted to a rigid shaft frame extending through the shaft 112. In any event, prior to, during, and/or after the tissue regions 278 and 280 have been tensioned, the electrodes 244 and 245 can be utilized to treat the tissue and the movable member 136 can be slid through the knife slots 260 and 260' defined in the first jaw 200 and the second jaw 202, respectively, to transect the tissue.

Figure 17:
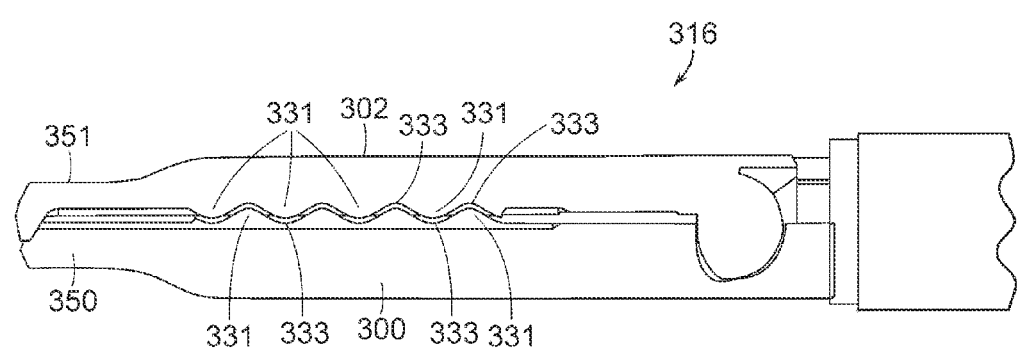
FIG. 17 is a side view of an end-effector comprising tissue-gripping portions in accordance with at least one non-limiting embodiment of the present disclosure.

In various embodiments, referring now to FIG. 17, an end effector of a surgical instrument, such as end effector 316, for example, can comprise a first jaw 300 and a second jaw 302 wherein each jaw 300, 302 can comprise a plurality of teeth configured to grip the tissue positioned intermediate the first jaw 300 and the second jaw 302. In at least one such embodiment, the teeth can be comprised of crests 331 which are separated by valleys 333 and can be defined in the first jaw frame 350 of the first jaw 300 and/or the second jaw frame 351 of the second jaw 302, for example.

While the present disclosure has been illustrated by description of several example embodiments and while the example embodiments have been described in considerable detail, it is not the intention of the applicants to restrict or in any way limit the scope of the appended claims to such detail. Additional advantages and modifications may be readily apparent to those of skill in the art. Furthermore, although the example embodiments disclosed herein have been described in connection with a surgical instrument, other embodiments are envisioned in connection with any suitable medical device. While this disclosure has been described as having exemplary designs, the disclosure may be further modified within the spirit and scope of the disclosure. This application is therefore intended to cover any variations, uses, or adaptations of the disclosure using its general principles. Further, this disclosure is intended to cover such departures from the present disclosure as come within known or customary practice in the art to which this disclosure pertains.

The various embodiments of the present disclosure have been described above in connection with cutting-type surgical instruments. It should be noted, however, that in other embodiments, the surgical instruments disclosed herein need not be a cutting-type surgical instrument. For example, it could be a non-cutting endoscopic instrument, a grasper, a stapler, a clip applier, an access device, a drug/gene therapy delivery device, an energy device using ultrasound, RF, laser, etc. In certain embodiments, an ultrasonic instrument can be utilized in accordance with the embodiments disclosed herein. In one such embodiment, an ultrasonic instrument can comprise a first portion comprising a handle portion and/or end effector, for example, and a second portion comprising radiation-sensitive electronics. Various ultrasonic instruments are disclosed in U.S. Pat. No. 6,063,098, entitled ARTICULATABLE ULTRASONIC SURGICAL APPARATUS, which issued on May 16, 2000, the entire disclosure of which is hereby incorporated by reference in its entirety. Although the present disclosure has been described herein in connection with certain disclosed embodiments, many modifications and variations to those embodiments may be implemented. For example, different types of end effectors may be employed. Also, where materials are disclosed for certain components, other materials may be used. The foregoing description and following claims are intended to cover all such modification and variations.

The disclosures of the following references are also incorporated by reference herein in their entireties:

*Heat-induced changes in the mechanics of a collagenous tissue: Isothermal free-shrinkage.* Chen, S. S., Wright, N. T., Humphrey, J. D., 1997. ASME Journal of Biomechanical Engineering 119, 372-378.

*Heat-induced changes in the mechanics of a collagenous tissue: Pseudoelastic behavior at 37° C.* Chen, S. S., Humphrey, J. D., 1998. Journal of Biomechanics 31, 211-216.

*Phenomenological evolution equations for heat-induced shrinkage of a collagenous tissue.* Chen, S. S., Wright, N. T., Humphrey, J. D., 1998b. IEEE Transactions on Biomedical Engineering 45, 1234-1240.

*Time-Temperature Equivalence of Heat-Induced Changes in Cells and Proteins.* Wright, N. T., Chen, S. S., Humphrey, J. D., 1998. ASME Journal of Biomechanical Engineering 120, 22-26.

*Altered mechanical behavior of epicardium under isothermal biaxial loading.* Wells P. B., Harris J. L., Humphrey J. D. J Biomech. Eng. 2004 August; 126(4):492-7.

*Altered mechanical behavior of epicardium due to isothermal heating under biaxial isotonic loads.* Harris J. L., Wells P. B., Humphrey J. D. Biomech. Eng. 2003 June; 125(3):381-8.

*Rate of shrinkage of tendon collagen—heat, entropy and free energy of activation of the shrinkage of untreated tendon. Effect of acid salt, pickle, and tannage on the activation of tendon collagen.* Weir, C. E., 1949. Journal of the American Leather Chemists Association 44, 108-140.

*Reversible and irreversible denaturation of collagen fibers.* Hormann, H., Schlebusch, H., 1971. Biochemistry 10, 932-937.

*Studies in thermal injury V. The predictability and the significance of thermally induced rate processes leading to irreversible epidermal injury.* Henriques, F. C., 1947. Archives of Pathology 43, 489-502.

*Thermal modification of collagen.* Wall, M. S.; Deng, X. H.; Torzilli, P. A.; Doty, S. B.; O'Brien, S. J.; Warren, R. F.; 1999. J. Shoulder Elbow Surg. 1999; 8:339-344.

*Thermally induced shrinkage of joint capsule.* Moran, K.; Anderson, P.; Hutcheson, J.; Flock, S.; 2000. Clinical Orthopaedics and Related Research; 381:248-255.

*A multi-sample denaturation temperature tester for collagenous biomaterials.* Lee, J. M., Pereira, C. A., Abdulla, D., Naimark, W. A., Crawford, I., 1995. Med. Eng. Phys. 1995; 17:115-121.

*The effect of thermal heating on the length and histologic properties of the glenohumeral joint capsule.* Hayashi, K., Thabit, III, G., Massa, K. L., Bogdanske, J. J., Cooley, A. J., Orwin, J. F., Markel, M. D., 1997. American Journal of Sports Medicine Vol. 25; 1:107-112.

*Thermal modification of connective tissues: Basic science considerations and clinical implications.* Arnoczky, S. P., Aksan, A., 2000. Journal of the American Academy of Orthopaedic Surgeons 2000; 8:305-313.

The surgical instruments disclosed herein can be designed to be disposed of after a single use, or they can be designed to be used multiple times. In either case, however, the surgical instruments can be reconditioned for reuse after at least one use. Reconditioning can comprise any combination of the steps of disassembly of the surgical instruments, followed by cleaning or replacement of particular pieces, and subsequent reassembly. In particular, the surgical instruments can be disassembled, and any number of the particular pieces or parts of the surgical instruments can be selectively replaced or removed in any combination. Upon cleaning and/or replacement of particular parts, the surgical instruments can be reassembled for subsequent use either at a reconditioning facility, or by a surgical team immediately prior to a surgical procedure. Those skilled in the art will appreciate that reconditioning of a surgical instrument can utilize a variety of techniques for disassembly, cleaning/replacement, and reassembly. Use of such techniques, and the resulting reconditioned surgical instrument, are all within the scope of the present disclosure.

Although the various embodiments of the devices have been described herein in connection with certain disclosed embodiments, many modifications and variations to those embodiments may be implemented. For example, different types of end effectors may be employed. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An end-effector configured to be attached to a surgical instrument comprising a closure beam, the end-effector comprising:

a first jaw comprising an electrode;
a second jaw, wherein at least one of the first jaw and the second jaw is movable relative to the other jaw between an open position and a closed position, and wherein, in the closed position, a first region of tissue is configured to be positioned intermediate the first jaw and the second jaw and is configured to be compressed;
the first jaw comprising:
a first slider member movably attached to the first jaw and movable relative to the electrode and to the closure beam, wherein the first slider member comprises a first tissue-contacting surface configured to engage a second region of tissue; and
the second jaw comprising:
a second slider member movably attached to the second jaw and movable relative to the electrode and to the closure beam, wherein the second slider member comprises a second tissue-contacting surface configured to engage the second region of tissue;
a longitudinal slot; and
a cutting member slidable within the longitudinal slot;
wherein the first slider member and the second slider member are configured to change the width of the end effector and apply a tensile stretching force to tissue positioned intermediate the first region of tissue and the second region of tissue when the first slider member and the second slider member are moved laterally relative to the electrode and to the longitudinal slot.

2. The end-effector of claim 1, wherein the electrode comprises:
a first end;
a second end positioned distal from the first end; and
an axis defined between the first end and the second end;
wherein the first slider member and the second slider member are movable laterally relative to the axis.

3. The end-effector of claim 1, wherein the electrode comprises:
a first end;
a second end positioned distal from the first end; and
an axis defined between the first end and the second end;
wherein the first slider member and the second slider member are movable away from the axis.

4. The end-effector of claim 1,
wherein the first jaw comprises:
a third slider member movably attached to the first jaw and movable relative to the electrode, wherein the third slider member comprises a third tissue-contacting surface configured to engage a third region of tissue; and
wherein the second jaw comprises:
a fourth slider member movably attached to the second jaw and movable relative to the electrode, wherein the fourth slider member comprises a fourth tissue-contacting surface configured to engage the third region of tissue, and wherein the third slider member and the fourth slider member are configured to apply a tensile force to tissue positioned intermediate the first region of tissue and the second region of tissue when the third slider member and the fourth slider member are moved relative to the electrode.

5. The end-effector of claim 1, comprising:
a proximal end;
a distal end positioned distal from the proximal end; and
a movable member configured to engage the first jaw and the second jaw when the movable member is advanced from the proximal end toward the distal end to compress the first region of the tissue, wherein the movable member is configured to bias the first slider member away from the electrode, and wherein the movable member is configured to bias the second slider member away from the electrode.

6. The end-effector of claim 1, comprising:
a proximal end;
a distal end positioned distal from the proximal end; and
an axis defined between the proximal end and the distal end;
wherein the first slider member and the second slider member are moveable relative to the axis between a first position and a second position, and wherein the second position is further away from the axis than the first position.

7. The end-effector of claim 1, comprising:
a biasing member positioned between the first slider member and a portion of the first jaw, wherein the biasing member is configured to bias the first slider member toward the electrode.

8. An end-effector configured to be attached to a surgical instrument, the end-effector comprising:
a first jaw comprising an electrode;
a second jaw, wherein at least one of the first jaw and the second jaw is movable relative to the other jaw between an open position and a closed position, and wherein, in the closed position, a first region of tissue is configured to be positioned intermediate the first jaw and the second jaw and is configured to be compressed;
the first jaw comprising:
　a first slider member movably attached to the first jaw and movable relative to the electrode, wherein the first slider member comprises a first tissue-contacting surface configured to engage a second region of tissue; and
　a third slider member movably attached to the first jaw and movable relative to the electrode, wherein the third slider member comprises a third tissue-contacting surface configured to engage a third region of tissue; and
the second jaw comprising:
　a second slider member movably attached to the second jaw and movable relative to the electrode, wherein the second slider member comprises a second tissue-contacting surface configured to engage the second region of tissue; and
　a fourth slider member movably attached to the second jaw and movable relative to the electrode, wherein the fourth slider member comprises a fourth tissue-contacting surface configured to engage the third region of tissue;
wherein the first slider member and the second slider member are configured to apply a tensile force to tissue positioned intermediate the first region of tissue and the second region of tissue when the first slider member and the second slider member are moved relative to the electrode;
wherein the third slider member and the fourth slider member are configured to apply a tensile force to tissue positioned intermediate the first region of tissue and the third region of tissue when the third slider member and the fourth slider member are moved relative to the electrode; and
wherein the first slider member and the second slider member are configured to move relative to the electrode in a first direction, wherein the third slider member and the fourth slider member are configured to move relative to the electrode in a second direction, and wherein the first direction is substantially opposite to the second direction.

9. An end-effector configured to be attached to a surgical instrument, the end-effector comprising:
a first jaw comprising an electrode;
a second jaw, wherein at least one of the first jaw and the second jaw is movable relative to the other jaw between an open position and a closed position, and wherein, in the closed position, a first region of tissue is configured to be positioned intermediate the first jaw and the second jaw and is configured to be compressed;
the first jaw comprising:
　a first slider member movably attached to the first jaw and movable relative to the electrode, wherein the first slider member comprises a first tissue-contacting surface configured to engage a second region of tissue; and
the second jaw comprising:
　a second slider member movably attached to the second jaw and movable relative to the electrode, wherein the second slider member comprises a second tissue-contacting surface configured to engage the second region of tissue;
wherein the first slider member and the second slider member are configured to apply a tensile force to tissue positioned intermediate the first region of tissue and the second region of tissue when the first slider member and the second slider member are moved relative to the electrode, and wherein the end-effector further comprises:
a proximal end configured to be engaged with the surgical instrument; and
a distal end positioned distal from the proximal end;
wherein the end-effector is configured to receive at least a portion of a movable member comprising a cam;
wherein the first slider member comprises:
　a first camming surface;
　a second camming surface; and
　a channel defined intermediate the first camming surface and the second camming surface; and
wherein the cam is configured to move within the channel, wherein the cam is configured to engage the first camming surface to move the first slider member away from the electrode, and wherein the cam is configured to engage the second camming surface to move the first slider member toward the electrode.

10. A surgical instrument, comprising:
a first jaw comprising an electrode;
a second jaw;
a movement means for moving at least one of the first jaw and the second jaw relative to the other jaw between an open position and a closed position to compress a first region of tissue positioned intermediate the first jaw and the second jaw;
the first jaw comprising:
　a first member movably attached to the first jaw and movable relative to the electrode and to the movement means, wherein the first member comprises a first tissue-contacting surface configured to grip a second region of tissue;
the second jaw comprising:
　a second member movably attached to the second jaw and movable relative to the electrode and to the movement means, wherein the second member comprises a second tissue-contacting surface configured to grip the second region of tissue; and a biasing means for biasing at least the first member relative to the electrode to expand the first jaw and to tension and stretch tissue positioned intermediate the first region of tissue and the second region of tissue.

11. A surgical instrument, comprising:
an elongate shaft comprising a proximal end and a distal end;
a handle portion extending from the proximal end of the elongate shaft;
a closure beam;
an end-effector extending from the distal end of the elongate shaft, the end-effector comprising:
   a first jaw comprising an electrode;
   a second jaw, wherein at least one of the first jaw and the second jaw is movable relative to the other jaw between an open position and a closed position, wherein, in the closed position, a first region of tissue is configured to be positioned intermediate the first jaw and the second jaw and is configured to be compressed;
   the first jaw comprising:
      a first slider member movably attached to the first jaw and movable relative to the electrode and to the closure beam, wherein the first slider member comprises a first tissue-contacting surface configured to engage a second region of tissue; and
   the second jaw comprising:
      a second slider member movably attached to the second jaw and movable relative to the electrode and to the closure beam, wherein the second slider member comprises a second tissue-contacting surface configured to engage the second region of tissue;
   a longitudinal slot; and
   a cutting member slidable within the longitudinal slot;
   wherein the first slider member and the second slider member are configured to change a shape of the first jaw and a shape of the second jaw and are configured to apply a tensile force to stretch tissue positioned intermediate the first region of tissue and the second region of tissue when the first slider member and the second slider member are moved relative to the electrode and away from the longitudinal slot.

12. The surgical instrument of claim 11,
wherein the electrode comprises:
   a first end;
   a second end positioned distal from the first end; and
   an axis defined between the first end and the second end;
wherein the first slider member and the second slider member are movable in a lateral direction relative to the axis.

13. The surgical instrument of claim 11,
wherein the electrode comprises:
   a first end;
   a second end positioned distal from the first end; and
   an axis defined between the first end and the second end;
wherein the first slider member and the second slider member are movable away from the axis.

14. The surgical instrument of claim 11,
wherein the first jaw comprises:
   a third slider member movably attached to the first jaw and movable relative to the electrode, wherein the third slider member comprises a third tissue-contacting surface configured to engage a third region of tissue;
wherein the second jaw comprises:
   a fourth slider member movably attached to the second jaw and movable relative to the electrode, wherein the fourth slider member comprises a fourth tissue-contacting surface configured to engage the third region of tissue, and wherein the third slider member and the fourth slider member are configured to apply a tensile force to tissue positioned intermediate the first region of tissue and the third region of tissue when the third slider member and the fourth slider member are moved relative to the electrode.

15. The surgical instrument of claim 11,
wherein the end-effector comprises:
   a proximal end; and
   a distal end positioned distal from the proximal end; and
wherein the closure beam comprises a movable member configured to engage the first jaw and the second jaw when the movable member is advanced from the proximal end toward the distal end, wherein the movable member is configured to bias the first slider member away from the electrode, and wherein the movable member is configured to bias the second slider member away from the electrode.

16. The surgical instrument of claim 11,
wherein the end-effector comprises:
   a proximal end; and
   a distal end positioned distal from the proximal end; and
wherein the closure beam comprises a movable member comprising a cutting member configured to cut the tissue, wherein the movable member is configured to engage the first jaw and the second jaw when the movable member is advanced from the proximal end toward the distal end, wherein the movable member is configured to act against the first slider member to move the first slider member relative to the electrode, and wherein the movable member is configured to act against the second slider member to move the second slider member relative to the electrode.

17. The surgical instrument of claim 11, wherein the end-effector comprises:
   a proximal end;
   a distal end positioned distal from the proximal end; and
   an axis defined between the proximal end and the distal end;
wherein the first slider member and the second slider member are moveable relative to the axis between a first position and a second position, and wherein the second position is further away from the axis than the first position.

18. The surgical instrument of claim 11, wherein the end-effector comprises a biasing member positioned between the first slider member and a portion of the first jaw, and wherein the biasing member is configured to bias the first slider member toward the electrode.

19. A surgical instrument comprising:
an elongate shaft comprising a proximal end and a distal end;
a handle portion extending from the proximal end of the elongate shaft;
an end-effector extending from the distal end of the elongate shaft, the end-effector comprising:
   a first jaw comprising an electrode;
   a second jaw, wherein at least one of the first jaw and the second jaw is movable relative to the other jaw between an open position and a closed position, wherein, in the closed position, a first region of tissue is configured to be positioned intermediate the first jaw and the second jaw and is configured to be compressed;

the first jaw comprising:
    a first slider member movably attached to the first jaw and movable relative to the electrode, wherein the first slider member comprises a first tissue-contacting surface configured to engage a second region of tissue; and the second jaw comprising:
    a second slider member movably attached to the second jaw and movable relative to the electrode, wherein the second slider member comprises a second tissue-contacting surface configured to engage the second region of tissue;

wherein the first slider member and the second slider member are configured to apply a tensile force to tissue positioned intermediate the first region and the second region when the first slider member and the second slider member are moved relative to the electrode, and wherein the surgical instrument further comprises:

a cutting member comprising a cam;

wherein the end-effector comprises:
    a proximal end; and
    a distal end positioned distal from the proximal end;
    wherein the first slider member comprises:
        a first camming surface;
        a second camming surface; and
        a channel defined intermediate the first camming surface and the second camming surface; and wherein the cam is configured to move into the channel, wherein the cam is configured to engage the first camming surface to move the first slider member away from the electrode, and wherein the cam is configured to engage the second camming surface to move the first slider member toward the electrode.

20. An end-effector, comprising:
a first jaw; and
a second jaw, wherein at least one of the first jaw and the second jaw is movable relative to the other jaw between an open position and a closed position, and wherein a a first region of tissue is configured to be compressed between the first jaw and the second jaw when at least one of the first jaw and the second jaw is in the closed position;
wherein the first jaw comprises:
    an electrode, comprising:
        a first end;
        a second end positioned distal from the first end; and
        a longitudinal axis defined between the first end and the second end; and
    a first slider member movably attached to the first jaw and movable laterally relative to the longitudinal axis, wherein the first slider member comprises a first tissue-contacting surface configured to engage a second region of the tissue;
wherein the second jaw comprises a second slider member movably attached to the second jaw and movable laterally relative to the longitudinal axis, wherein the second slider member comprises a second tissue-contacting surface configured to engage the second region of the tissue; and
wherein the first slider member and the second slider member are configured to extend the end-effector and apply a tensile force to stretch tissue positioned intermediate the first region of tissue and the second region of tissue when the first slider member and the second slider member are moved laterally relative to the longitudinal axis.

\* \* \* \* \*